US012765748B2

(12) United States Patent
Bogusky et al.

(10) Patent No.: US 12,765,748 B2
(45) Date of Patent: Oct. 20, 2026

(54) SYSTEMS AND METHODS FOR USE OF A VARIABLE STIFFNESS FLEXIBLE ELONGATE DEVICE

(71) Applicant: INTUITIVE SURGICAL OPERATIONS, INC., Sunnyvale, CA (US)

(72) Inventors: Joseph D. Bogusky, San Jose, CA (US); Kyle R. Miller, San Jose, CA (US); Randall L. Schlesinger, San Mateo, CA (US); Serena H. Wong, Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 545 days.

(21) Appl. No.: 18/311,424

(22) Filed: May 3, 2023

(65) Prior Publication Data

US 2023/0301493 A1 Sep. 28, 2023

Related U.S. Application Data

(63) Continuation of application No. 16/522,569, filed on Jul. 25, 2019, now Pat. No. 11,678,788.
(Continued)

(51) Int. Cl.
*A61B 1/00* (2006.01)
*A61B 1/005* (2006.01)
(Continued)

(52) U.S. Cl.
CPC ...... *A61B 1/00078* (2013.01); *A61B 1/00147* (2013.01); *A61B 1/0052* (2013.01);
(Continued)

(58) Field of Classification Search
CPC . A61B 1/00154; A61B 1/00078; A61B 1/008; A61B 1/009; A61M 2025/0681; A61M 2025/0161
See application file for complete search history.

(56) References Cited

U.S. PATENT DOCUMENTS 3,552,384 A 1/1971 Pierie et al.
5,251,611 A 10/1993 Zehel et al.
(Continued)

FOREIGN PATENT DOCUMENTS

CN 107921236 A 4/2018
WO WO-2013056006 A2 4/2013
(Continued)

OTHER PUBLICATIONS

Office Action for Chinese Application No. CN201980026303, mailed Aug. 25, 2024, 20 pages.
(Continued)

*Primary Examiner* — Deanna K Hall
(74) *Attorney, Agent, or Firm* — Haynes & Boone, LLP.

(57) ABSTRACT

The following describes various applications and uses for a controllably rigidizable flexible, device or sheath, Such rigidizing mechanisms can allow for a transition between a rigid state and a flexible state of a sheath. Rigidization can be applied along an entire length of a flexible sheath or along select portions of the sheath, and the rigidization can be of varying stiffness. Rigidization can be user controlled or automatically controlled using computer processes.

20 Claims, 23 Drawing Sheets

Related U.S. Application Data

(60) Provisional application No. 62/703,263, filed on Jul. 25, 2018.

(51) Int. Cl.

| | |
|---|---|
| ***A61B 1/307*** | (2006.01) |
| ***A61B 5/06*** | (2006.01) |
| ***A61M 16/04*** | (2006.01) |
| ***A61M 25/01*** | (2006.01) |

(52) U.S. Cl.

CPC .............. *A61B 1/009* (2022.02); *A61B 1/307* (2013.01); *A61B 5/065* (2013.01); *A61M 16/0488* (2013.01); *A61M 25/0113* (2013.01); *A61M 2025/0166* (2013.01); *A61M 2210/005* (2013.01); *A61M 2210/0625* (2013.01); *A61M 2210/1032* (2013.01); *A61M 2210/1053* (2013.01); *A61M 2210/1057* (2013.01)

(56) References Cited

U.S. PATENT DOCUMENTS

| | | | | |
|---|---|---|---|---|
| 5,759,151 | A | 6/1998 | Sturges | |
| 6,380,732 | B1 | 4/2002 | Gilboa | |
| 6,389,187 | B1 | 5/2002 | Greenaway et al. | |
| 6,610,007 | B2 * | 8/2003 | Belson .................. | A61B 1/015 604/95.01 |
| 6,974,411 | B2 | 12/2005 | Belson | |
| 7,316,681 | B2 | 1/2008 | Madhani et al. | |
| 7,772,541 | B2 | 8/2010 | Froggatt et al. | |
| 7,914,466 | B2 | 3/2011 | Davis et al. | |
| 8,900,131 | B2 | 12/2014 | Chopra et al. | |
| 9,138,166 | B2 | 9/2015 | Wong et al. | |
| 9,259,274 | B2 | 2/2016 | Prisco | |
| 9,452,276 | B2 | 9/2016 | Duindam et al. | |
| 10,737,073 | B2 | 8/2020 | Barrish et al. | |
| 11,678,788 | B2 | 6/2023 | Bogusky et al. | |
| 2006/0013523 | A1 | 1/2006 | Childlers et al. | |
| 2013/0096385 | A1 | 4/2013 | Fenech et al. | |
| 2017/0021132 | A1 | 1/2017 | Laby et al. | |
| 2018/0056040 | A1 | 3/2018 | Fenech et al. | |
| 2021/0268233 | A1 | 9/2021 | Bogusky et al. | |

FOREIGN PATENT DOCUMENTS

| | | | |
|---|---|---|---|
| WO | WO-2015061692 | A1 | 4/2015 |
| WO | WO-2016160586 | A1 | 10/2016 |
| WO | WO-2016191298 | A1 | 12/2016 |
| WO | WO-2017044874 | A1 | 3/2017 |
| WO | WO-2017139591 | A1 | 8/2017 |
| WO | WO-2017139621 | A1 | 8/2017 |
| WO | WO-2018005928 | A1 | 1/2018 |
| WO | WO-2018145100 | A1 | 8/2018 |
| WO | WO-2019246240 | A1 | 12/2019 |

OTHER PUBLICATIONS

International Preliminary Report on Patentability for Application No. PCT/2019/037954, mailed on Dec. 30, 2020, 08 pages.

International Search Report and Written Opinion for Application No. PCT/US2019/037954, mailed on Sep. 30, 2019, 13 pages.

Vertut, J, and Coiffet, P., “Robot Technology: Teleoperation and Robotics Evolution and Development,” English translation, Prentice-Hall, Inc., Inglewood Cliffs, NJ, USA 1986, vol. 3A, 332 pages.

* cited by examiner

SYSTEMS AND METHODS FOR USE OF A VARIABLE STIFFNESS FLEXIBLE ELONGATE DEVICE

CROSS REFERENCE TO RELATED APPLICATIONS

This application is a continuation of U.S. Pat. No. 16,522,569 filed Jul. 25, 2019, which claims the benefit of U.S. Provisional Patent Application Ser. No. 62/703,263 filed Jul. 25, 2018, the disclosures of which are expressly incorporated herein by reference.

TECHNICAL FIELD

The present disclosure is directed to teleoperated systems and in particular teleoperated systems involving use of flexible elongate devices.

BACKGROUND

Flexible elongate devices can be employed in range of fields needing access to restricted openings such as for the exploration of pipes or in medical procedures, especially minimally invasive medical techniques.

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions physician may insert minimally invasive medical instruments (including surgical, diagnostic, therapeutic, or biopsy instruments) to reach a target tissue location.

One such minimally invasive technique is to use a flexible and/or steerable elongate device, such as a flexible catheter, that can be inserted into anatomic passageways and navigated toward a region of interest within the patient anatomy, in some applications, the flexible and/or steerable elongate device needs to be held in a particular shape to enable or improve the safety of a procedure. It would be advantageous to provide improvements to systems and methods for holding a flexible elongate device in a desired pose.

SUMMARY OF THE INVENTION

Embodiments of the present invention have a range of advantages. For example, in the environment of articulating devices that navigate the tortuosity of human anatomy, it advantageous to securely hold the contorted position of said device while instruments are being delivered through the device. Frequently, devices that pass through an articulating device will exert forces that have a tendency to straighten a contorted and articulated portion of the device, Embodiments of the invention provides various apparatus and methods to hold the pose of a catheter in a contorted position for stable delivery of instruments.

A first aspect of the disclosure provides a system comprising an elongate device having a proximal end, a distal end, and a plurality of segments positioned along a length of the elongate device between the proximal end and the distal end. The system comprising a processor configured to monitor insertion of the elongate device relative to a reference location. The processor configured to maintain each of the plurality of segments that are proximal to the reference location in a first rigidity state. The processor configured to transition each of the plurality of segments that are distal to the reference location to a second rigidity state as the elongate device is inserted.

In some implementation of the first aspect of the disclosure, the elongate device is steerable.

In some implementation of the first aspect of the disclosure, each of the plurality of segments includes a stiffening mechanism to alter rigidity of the each of the plurality of segments.

In some implementation of the first aspect of the disclosure, the second rigidity state is less rigid than the first rigidity state.

In some implementation of the first aspect of the disclosure, the reference location is near an entry point to patient anatomy. The entry point is at a natural opening of the patient anatomy or an incision in the patient anatomy.

In some implementation of the first aspect of the disclosure, the system further comprises a sensor for monitoring the insertion of the elongate device.

In some implementation of the first aspect of the disclosure, the system further comprises a first insertion device movable along an insertion direction and coupled to the elongate device.

In some implementation of the first aspect of the disclosure, the elongate device includes a lumen that extends from the proximal end of the elongate device to the distal end of the elongate device and through each of the plurality of segments.

In some implementation of the first aspect of the disclosure, the system further comprises a flexible elongate instrument having a proximal portion and a steerable distal end, wherein the flexible elongate instrument is slidably disposed within the lumen.

In some implementation of the first aspect of the disclosure, the system further comprises a first insertion device movable along an insertion direction and coupled to the elongate device. The system also comprises a second insertion device movable along the insertion direction and coupled to the flexible elongate instrument. The first insertion device provides independent insertion movement from insertion movement of the second insertion device.

A second aspect of the disclosure provides a method of using an elongate, variable stiffness device having a proximal end, a distal end, and a plurality of segments positioned along a length of the variable stiffness device. Each of the plurality of segments is individually configurable between a rigid state and a flexible state. The method comprises monitoring insertion of the elongate instrument relative to a first reference location. The method comprises maintaining a first set of the plurality of segments in a first state, wherein the first set of the plurality of segments are proximal to the first reference location. The method comprises transitioning a second set of the plurality of segments to a second state, wherein the second set of the plurality of segments are distal to the first reference location.

In some implementation of the second aspect of the disclosure, the first state is a rigid state and the second state is a less rigid state than the first state.

In some implementation of the second aspect of the disclosure, the first reference location is near an entry point to a patient anatomy and the entry point is at a natural opening of the patient anatomy or at an incision in the patient anatomy.

In some implementation of the second aspect of the disclosure, the method further comprises monitoring insertion of the elongate instrument relative to a second reference location, wherein the second reference location is distal to the first reference location. The method further comprises transitioning a third set of the plurality of segments to a third state. The third set of the plurality of segments are between the first reference location and the second reference location.

In some implementation of the second aspect of the disclosure, the method further comprises compressing the third set of the plurality of segments.

In some implementation of the second aspect of the disclosure, the first state is a rigid state, the second state is a less rigid state than the first state, and the third state is a less rigid state than the second state.

In some implementation of the second aspect of the disclosure, the second reference location is at an entry point to a patient anatomy and the first reference location is outside of patient anatomy.

In some implementation of the second aspect of the disclosure, the first reference location is at an entry point to a patient anatomy, and the second reference location is within the patient anatomy.

In some implementation of the second aspect of the disclosure, the first reference is near a mouth of a patient and the second location is within a trachea of the patient.

BRIEF DESCRIPTIONS OF THE DRAWINGS

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances, well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, v-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
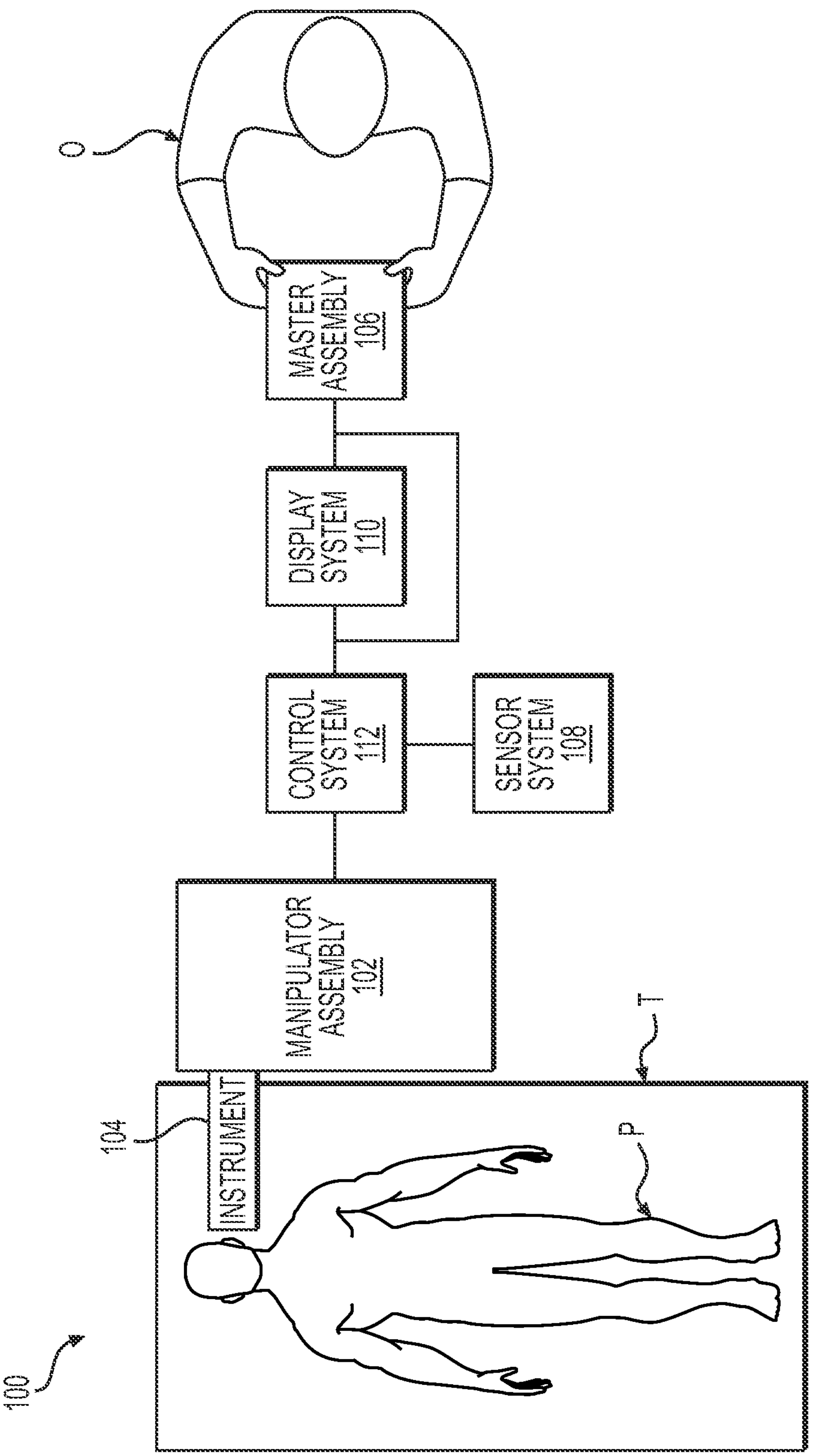
FIG. 1 is a simplified diagram of a teleoperated medical system according to some embodiments.

FIG. 1 is a simplified diagram of a medical system 100 according to some embodiments. In some embodiments, medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 1, medical system 100 generally includes a manipulator assembly 102 for operating a medical instrument 104 in performing various procedures on a patient P. The manipulator assembly 102 may be teleoperated, non-teleoperated, or a hybrid teleoperated and non-teleoperated assembly with select degrees of freedom of motion that may be directly driven and/or teleoperated and select degrees of freedom of motion that may be non-motorized. Manipulator assembly 102 is mounted to or near an operating table T. A master assembly 106 allows an operator O (e.g., a surgeon, a clinician, or a physician as illustrated in FIG. 1) to view the interventional site and to control manipulator assembly 102. Master assembly 106 generally includes one or more control devices for controlling manipulator assembly 102.

Medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some examples, control system 112 may transmit signals instructing one or more actuators of manipulator assembly 102 to move medical instrument 104. Manipulator assembly 102 supports medical instrument 104 and may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes), in three degrees of rotational motion (e.g., rotation about the X, Y, Z Cartesian axes), and in bend, e.g. pitch and yaw about a longitudinal axis of the medical instrument 104. Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Medical system 100 may include a sensor system 108 with one or more sub-systems for receiving information about the instruments of manipulator assembly 102. Such sub-systems may include a position/location sensor system (e.g., art electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Medical system 100 also includes a display system 110 for displaying an image or representation of the surgical site and medical instrument 104 generated by sub-systems of sensor system 108. Display system 110 may present images of a surgical site recorded preoperatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. In some embodiments, often for purposes of imaged guided surgical procedures, display system 110 may display a virtual navigational image in which the actual location of medical instrument 104 is registered (i.e., dynamically referenced) with and displayed within the preoperative or concurrent images/model, as will be described. Art image of a portion of medical instrument 104 or other graphical or alphanumeric indicators may be superimposed on the virtual image to assist operator O in the control of medical instrument 104.

During a virtual navigation procedure, sensor system 108 may be used to compute an approximate location of medical instrument 104 with respect to the anatomy of patient 1'. The location can be used to produce both macro-level (external) tracking images of the anatomy of patient P and virtual internal images of the anatomy of patient. I'. The system may implement one or more electromagnetic (EM) sensor, fiber optic sensors, and/or other sensors to register and display a medical implement together with preoperatively recorded surgical images, such as those from a virtual visualization system. For example, PCT Publication WO 2016/191298 (published. Dec. 1, 2016) (disclosing "Systems and Methods of Registration for Image Guided Surgery"), which is incorporated by reference herein in its entirety, discloses such one system. Control system 112 may optionally include a virtual visualization system to provide navigation assistance to operator O when controlling medical instrument 104 during an image-guided surgical procedure. In some implementations, movements of the medical instrument 104 are automatically completed by the control system 112 following a pre-planned path or using sensors to automatically drive through anatomy. Accordingly, motion, navigation, or sliding of the medical instrument in the patient anatomy is performed by the control system 112.

Figure 2A:
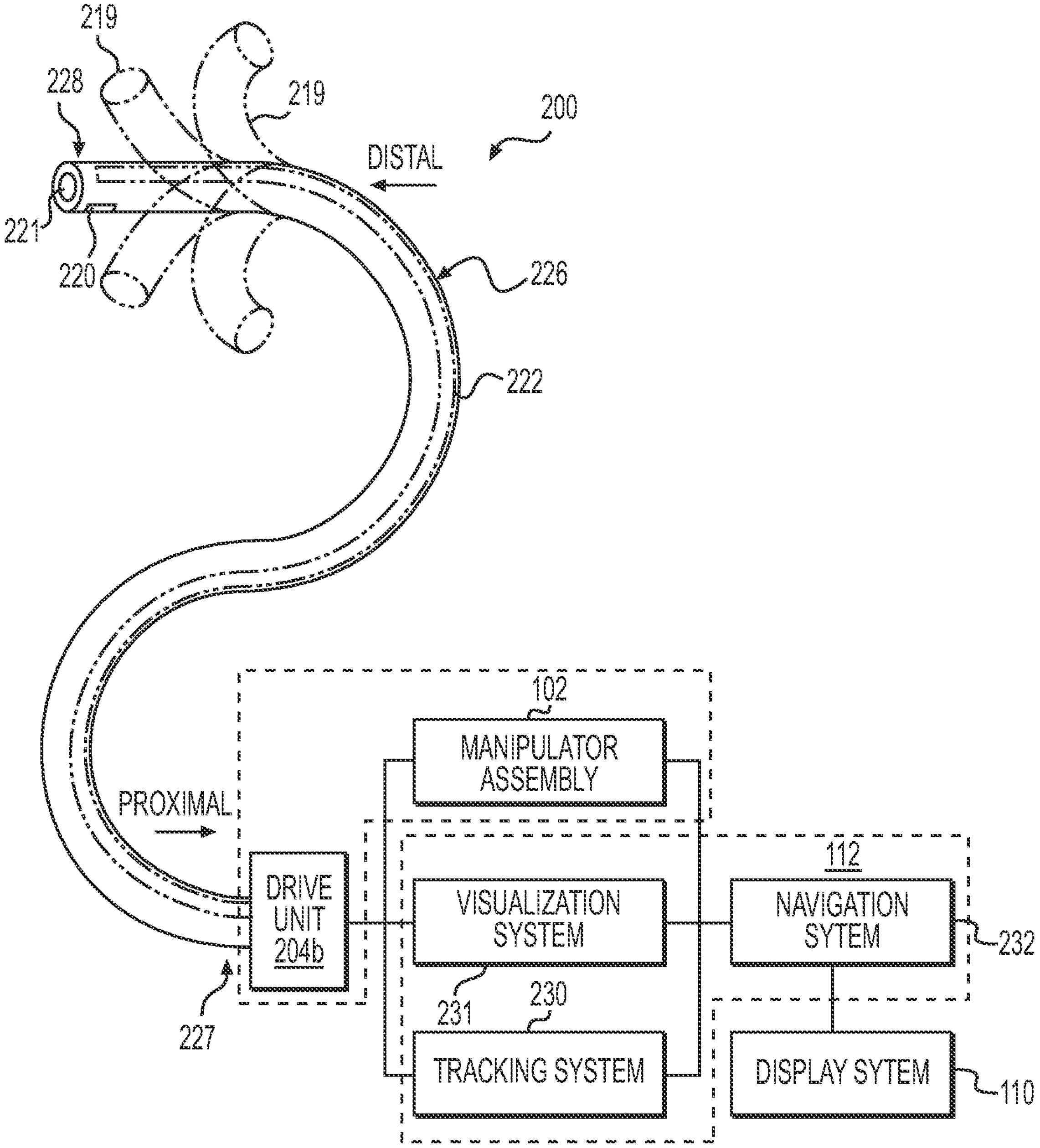
FIG. 2A is a simplified diagram of a steerable elongate device system according to some embodiments.

FIG. 2A is a simplified diagram of a medical instrument system 200 according to some embodiments. Medical instrument system 200 may be substantially similar in construction and function to medical system 100 except where described herein. Similarly to medical system 100, medical instrument system 200 may include display system 110, control system 112, and manipulator assembly 102 for operating medical instrument 104 (e.g. medical instrument 226). Medical instrument 226 may be an elongate device, such as a steerable flexible catheter, including a flexible body having proximal end portion 227 and distal end or tip portion 228. In some embodiments, control system 112 includes a visualization system 231, a navigation system 232, and a tracking system 230.

Tracking system 230 may optionally be implemented as hardware, firmware, software or a combination thereof which interact with or are otherwise executed by one or more computer processors, which may include the processors of control system 112 in FIG. 1, and may be used for determining the position, orientation, speed, velocity, pose, external forces, and/or shape of distal end portion 228 and/or of one or more segments along elongate device 226 using one or more sensors and/or imaging devices as described in further detail below.

Tracking system 230 may optionally track distal end 228 and/or one or more of the segments of elongate device 226 using a shape sensor 222. Shape sensor 222 may optionally include an optical fiber aligned with elongate device 226 (e.g., provided within an interior channel (not shown) or mounted externally). The optical fiber of shape sensor 222 forms a fiber optic bend sensor for determining the shape of elongate device 226. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. In some embodiments, tracking system 230 may optionally and/or additionally track distal end 228 using a position sensor system 220. Position sensor system 220 may be a component of an EM sensor system with position sensor system 220 including one or more conductive coils that may be subjected to an externally generated electromagnetic field. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some examples, a series of positional sensors (not shown), such as electromagnetic (EM) sensors similar to the sensors in position sensor 220 may be positioned along elongate device 226 and then used for shape sensing.

Figure 2B:
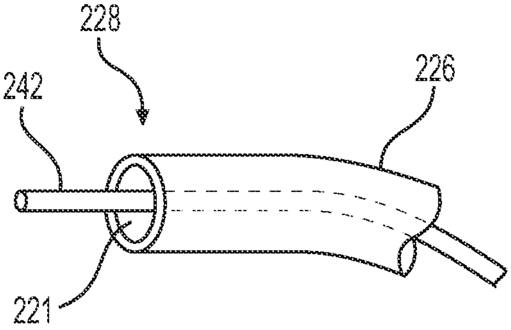
FIG. 2B is a simplified diagram of the steerable elongate device with a medical instrument extended according to some embodiments.

Elongate device 226 can include a working lumen or channel 221 sized and shaped to receive a medical instrument 242. In some implementations, the medical instrument 242 may be on a separate insertion axis than the elongate device 226. FIG. 2B is a simplified diagram of elongate device 226 with medical instrument 242 extended according to some embodiments. In some embodiments, medical instrument 242 may be used for procedures such as surgery, biopsy, ablation, illumination, irrigation, or suction. In various implementations, medical instrument 242 may be a steerable catheter (e.g., robotically or manually steerable), which in turn includes a working lumen for receiving a further medical instrument for performing a medical procedure.

Elongate device 226 may also house cables, linkages, or other steering controls (not shown) that extend between manipulator assembly 102 and distal end 228 to controllably bend distal end 228 as shown, for example, by broken dashed line depictions 219 of distal end 228. Steerable elongate devices are described in detail Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties. In embodiments in which medical instrument system 200 is actuated by a teleoperational assembly, manipulator assembly 102 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 226 may be steerable or, alternatively, the system may be non-steerable with no integrated mechanism for operator control of the bending of distal end 228. In some examples, one or more lumens, through which medical instruments can be deployed and used at a target surgical location, are defined in the walls of elongate device 226.

The information from tracking system 230 may be sent to a navigation system 232 where it is combined with information from visualization system 231 and/or the preoperatively obtained models (e.g., anatomic models of the patient anatomy) to provide the physician or other operator with real-time position information. In some examples, the real-time position information may be displayed on display system 110 of FIG. 1 for use in the control of medical instrument system 200. In some examples, control system 112 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 2C:
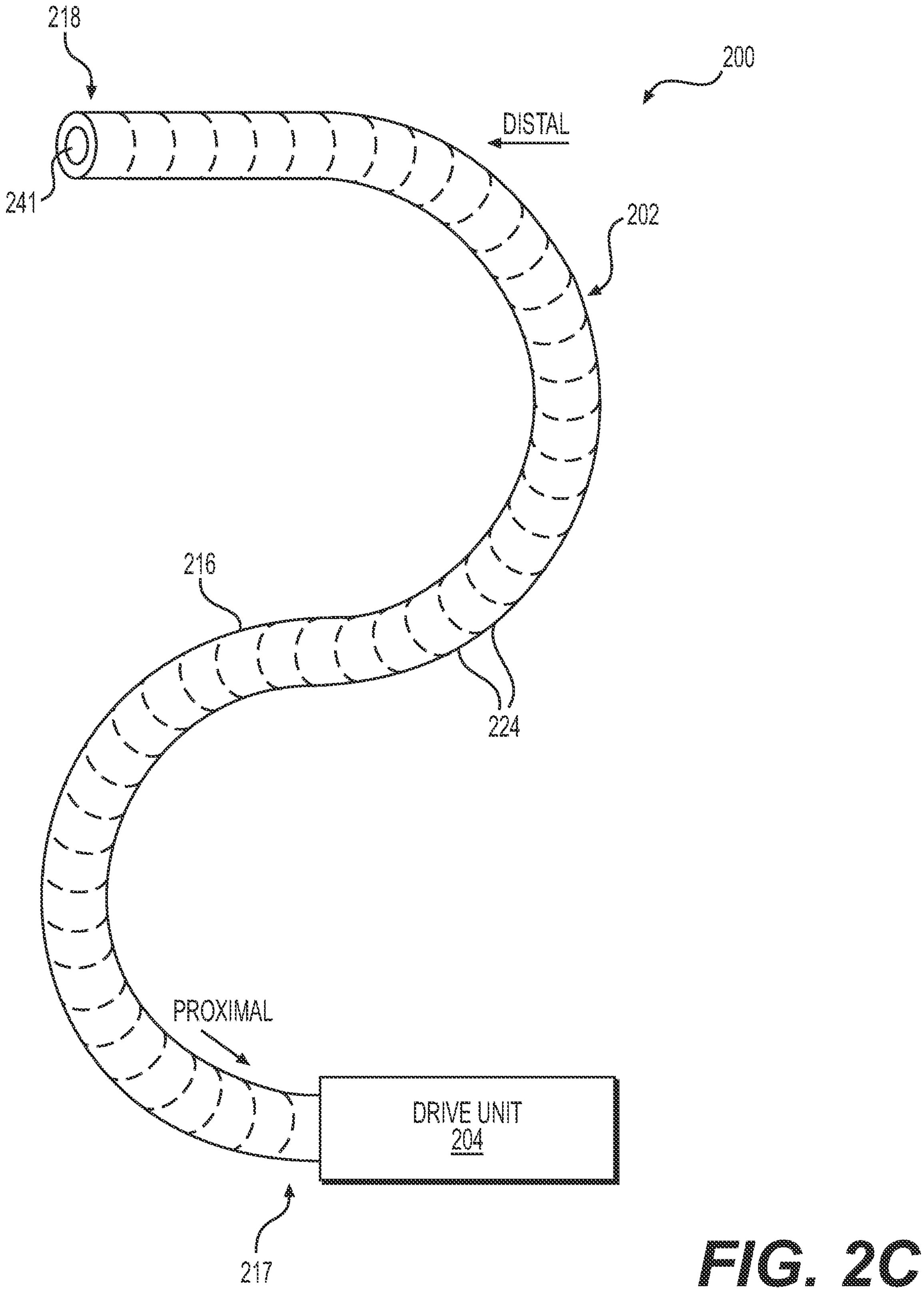
FIG. 2C is a simplified diagram of a segmented rigidizable elongate sheath according to some embodiments.

FIG. 2C is a simplified diagram of a segmented elongate sheath 202 according to some embodiments. The elongate sheath 202 may include a flexible body 216 having a distal end 218, a proximal end 217, a lumen 241 extending therebetween, and a plurality of segments 224 dividing a portion of or the entire length of the flexible body 216. A drive unit. 204, positioned at proximal end 217, may be coupled to the elongate sheath 202. Flexible body 216 may also house one or more stiffening mechanisms or systems that may be selectively actuated to assist or enable holding a pose or shape of the flexible body 216. Stiffening mechanisms are described in detail in P.C.T. Patent Application PCT/US2019/037954, filed Jun. 19, 2019, disclosing "Systems and Methods for Holding a Flexible Elongate Device In a Pose", which is incorporated by reference herein in its entirety. For example, one or more of the stiffening mechanisms may include a balloon configured to engage a support structure of the flexible body 216. The balloon can be configured to extend in between sub-elements of the support structure due to the application of an inflation pressure or vacuum from a pump (not shown) to maintain a portion of the flexible body 216 in a desired pose. In another example, one or more of the stiffening mechanisms may include a plurality of nitinol wires embedded in a wall structure of the flexible body 216. The plurality of nitinol wires may be distributed circumferentially around the working lumen 221. Selective activation or energizing of the nitinol wires causes them to engage—by changing their length—a portion of the flexible body 216 to hold or change its pose. Other stiffening mechanisms are contemplated by this disclosure. For example, the stiffening mechanisms may be provided by one or more control wires that can be controllably altered in tension to maintain a desired pose.

A stiffening mechanism may be positioned in each of a plurality of the segments 224 along flexible body 216 for individually selectively rigidizing each of the plurality of segments 224, providing for control-ably variable stiffness along the length of the flexible body. Accordingly, the elongate sheath 202 may be referred to throughout this disclosure as a variable stiffness device, variable stiffness elongate device, a segmented stiffness elongate device, discrete stiffness elongate device, or a variably rigidizeable elongate device. In various implementations, a stiffening mechanism may extend across a group of more than one of the plurality of segments 224 along flexible body 216 for individually selectively rigidizing the group of segments 224. A plurality of such groups may extend along the length of the flexible body 216. Accordingly, each of the plurality of segments 224 is configurable, either on an individual basis or as part of a group of segments, between a rigid state and a flexible state based on actuation of a corresponding stiffening mechanism. More generally, each of the stiffening mechanisms is individually selectively actuated to stiffen a discrete portion of the flexible body 216 along the length of the flexible body 216.

The state of the flexible body 216 may be one of a plurality of rigid states or a plurality of flexible states along a spectrum from partially rigid to fully rigid or partially flexible to fully flexible. In other words, the actuation of the stiffening mechanism may be modulated to provide differing amounts of rigidity to different ones of the segments 224, providing for a variable rigidity along the length of the flexible body 216. For example, inflation pressure or vacuum may be applied to a balloon to engage a particular section of the flexible body 216, of the flexible body 216 while less inflation pressure or vacuum may be applied to a separate set of balloons to engage a second section of the flexible body 216, and no inflation pressure or vacuum may be applied to a different set of balloons to engage a third section of the flexible body 216. Likewise, more or less energy may be applied to one or more of the nitinol wires. The fully rigid state corresponds to a maximum rigidity able to be provided by the stiffening mechanism. The variable rigid or variable flexible state along the length of the flexible body may be controlled using drive unit 204. The drive unit can be coupled to a controller, such as control system 112 or a separate controller or processor, to provide actuation for stiffening mechanisms, e.g. inflation pressure or vacuum to activate balloons or current to activate nitinol wires. Upon the drive unit 204 configuring actuation of the stiffening mechanism from a flexible state to a rigid state to rigidize a segment 224, the rigidity of the stiffening mechanism increases to a more rigid state than a prior configuration of the stiffening mechanism. Upon the drive unit 204 configuring actuation of the stiffening mechanism from a rigid state to a flexible state to cause a segment 2:24 to be more flexible, the rigidity of the stiffening mechanism decreases to a more flexible state than a prior configuration of the stiffening mechanism.

The stiffening mechanisms may be part of the steering controls, may be separately actuated, and/or may themselves also enable steering of the elongate device 20:2, For example, the drive unit 204 may control individual actuation and operation of each of the stiffening mechanisms. In some embodiments, the elongate device 202 may include sensor systems, such as shape sensor 222 in the form of an optical fiber, position sensor 220 in the form of a plurality of EM sensors distributed along the length of the flexible body 216, and/or a plurality of force sensors distributed along the length of the flexible body 216. Thus, the stiffening mechanisms may use information from the sensor systems to inform the control system 112 which then controls formation and holding of a shape of the flexible body 216, In some embodiments, the sensor systems may indicate a bend in elongate device 202 which exceeds a threshold and may be an indication of an unwanted effect, such as buckling of the elongate device 202 or buckling of the steerable medical instrument 226. The stiffening mechanisms may then be actuated only along the length of areas of detected buckling, to help prevent or alter a buckled state of the elongate device 202 and/or the medical instrument 226. In some embodiments, the buckled state is detected within the medical instrument 226 and the elongate device 202 is actuated to a rigid or flexible state along the length of the elongate device 202 which corresponds to the detected buckling of the medical instrument 226. Accordingly, the elongate device 202 can be used to support the medical instrument 226 as buckling begins, or can be used to correct buckling and help straighten the medical instrument 226.

In various implementations, the elongate device 226 may be a steerable catheter as described with reference to FIG. 2A, which in turn includes the working lumen 221 for receiving a further medical instrument (not shown) for performing a procedure (e.g., surgery, biopsy, ablation, illumination, irrigation, or suction). Throughout this disclosure, the elongate device 226 may variously be referred to as a steerable medical instrument 226. The elongate device 202 may be a passive sheath with stiffening mechanisms provided in segments 224 along the length of the elongate device 202 (as shown in FIG. 2B) and the steerable medical instrument 226 may be carried within the lumen 241 of the elongate device 202 and used to initially position the elongate device 202 in a flexible state. Subsequently, the elongate device 202 may be stiffened in a variable fashion along the length of the flexible body 216 to provide support for further positioning of the medical device 226. In alternative examples, the elongate device 20:2 may be steerable using similar mechanisms used for the medical instrument 226 as described in reference to FIG. The elongate device 202 may be positioned in a flexible state then subsequently the variable stiffness mechanisms may be actuated to provide support for delivery of the medical instrument 226 which may be passive, manually steerable, or robotically steerable. In other examples, the elongate device 202 may be housed within the working lumen 221 of the medical instrument 226. In either case, relative motion of the elongate device 202 with respect to the medical instrument 226 or vice versa may be referred to as telescopic operation.

Use of a Variable Stiffness Flexible Elongate Device in A Manipulator Assembly

Figure 3A:
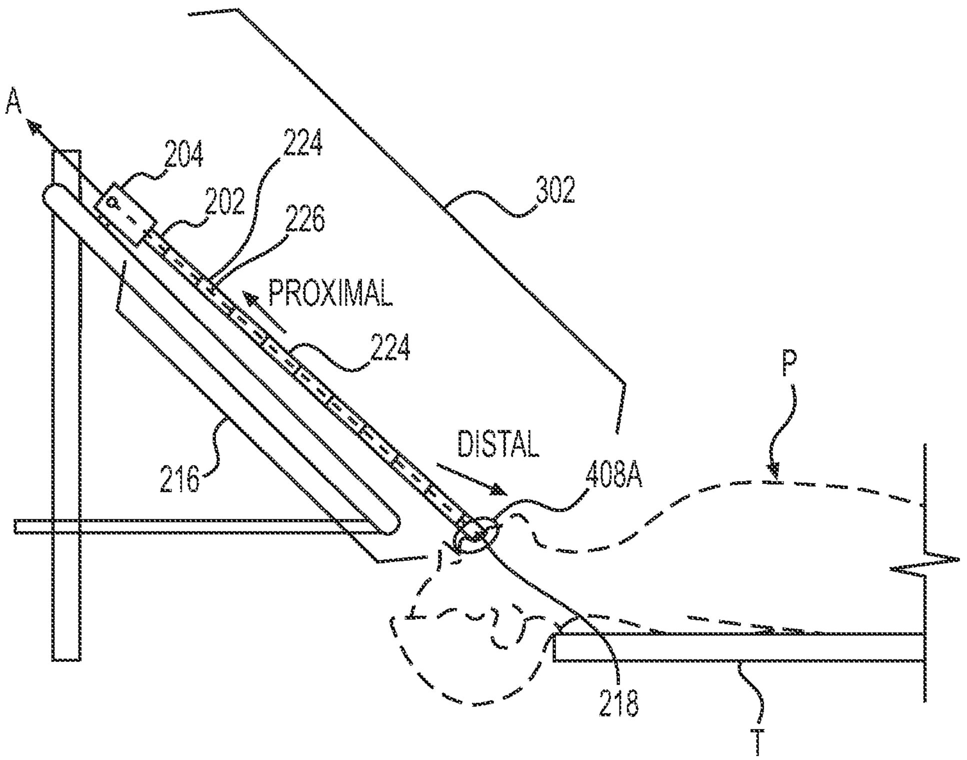
FIG. 3A-3B are simplified diagrams of a manipulator assembly for use with stiffening mechanisms of the segmented rigidizable elongate sheath according to some embodiments.
Figure 3B:
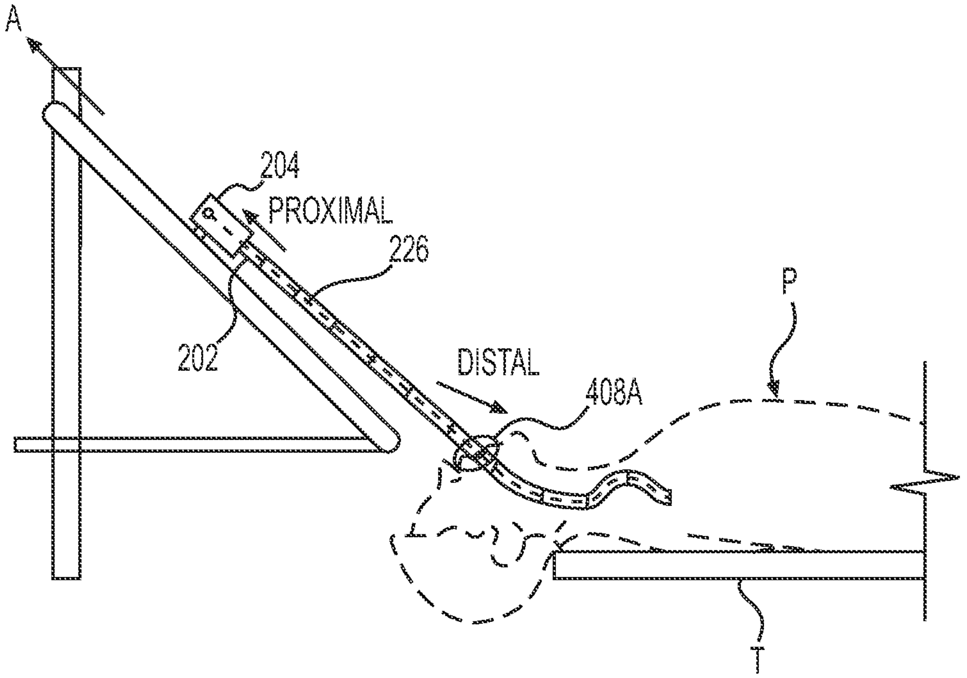

FIG. 3A-3B are simplified diagrams of a manipulator assembly 302 for use with the stiffening mechanisms of the elongate device 202. FIG. 3A illustrates a distal end 218 of the elongate device 202 positioned at a patient entry point (e.g. a patient mouth, pharynx, larynx, esophagus, or any other natural orifice or surgical incision entry point) while FIG. 3B illustrates the elongate device 202 inserted into patient anatomy. The manipulator assembly 302 includes the drive unit 204 coupled to a proximal portion of elongate device 202. Manipulator assembly 302 may be configured to facilitate insertion or retraction of elongate device 202 along an insertion axis A, into and from a patient anatomy in a distal direction or proximal direction as indicated in FIG. 3A-3B. Manipulator assembly 302 may be similar in structure and function as manipulator assembly 102 of FIG. 1 and may be coupled to a control system, such as control system 112 which may actuate insertion/retraction of elongate device 202 as well as actuate stiffening mechanisms in segments 224, using drive unit 204.

As illustrated in FIGS. 3A-3B, a reference location 408*a* may be provided indicating a transition point of entry for elongate device 202. In the example illustrated in FIGS. 3A-3B, the transition point is an entry point into patient anatomy, e.g. patient mouth. During insertion of the elongate device 202, a portion of flexible body 216 of elongate device 202 proximal to the reference location 408*a* is unsupported while, as illustrated in FIG. 3B a portion of the flexible body 216 distal of the reference location 408*a*, is supported by patient anatomy. Accordingly, the unsupported portion of the flexible body 216 proximal to the reference location 408*a*, can tend to buckle during insertion of the drive unit 204. Thus, reference location 408*a* can be used as a stationary point relative to the patient for dividing the elongate device 202 into a varying proximal and distal sections of the elongate device 202 as the elongate device 202 is inserted or retracted. For example, the proximal section of the elongate device 202 is positioned between the drive unit 204 and the reference location 408*a*. Likewise, the distal section of the elongate device 202 is positioned between the reference location 408*a* and the distal end 218 of the elongate device 202.

During movement of the drive unit 204 along the insertion axis A, one or more of the segments 224 pass by the reference location 408*a*. The configuration of the stiffening mechanism for the segment 224 is modulated by the drive unit 204 as the segment 224 passes the reference location 408*a*. For example, during movement of the drive unit 204 towards the patient P, as the segment 224 passes the reference location 408*a*, the segment 224 transitions from being on the proximal section to the distal section of the elongate device 202. Accordingly, the drive unit 204 configures actuation of the stiffening mechanism to transition from a rigid state to a flexible state (e.g., become more flexible), In another example, during movement of the instrument carriage 406 away from the patient P, as the segment 224 passes the reference location 408*a*, the segment transitions from being on the distal section to the proximal section of the elongate device 202. Accordingly, the drive unit 204 configures actuation of the stiffening mechanism for the segment 224 to transition from a flexible state to a rigid state (e.g., become more rigid).

Figure 4A:
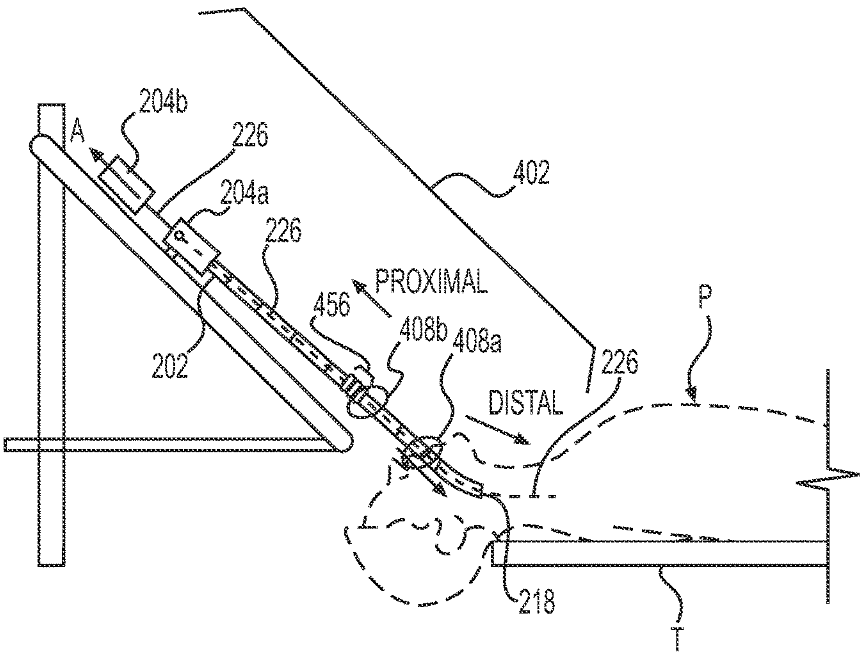
FIG. 4A is a simplified diagram of a manipulator assembly for use with the segmented rigidizable, elongate sheath and the steerable elongate device according to some embodiments.

FIG. 4A is a simplified diagram of a manipulator assembly 402 for use with elongate device 202 and medical instrument 226. The manipulator assembly 402 may be substantially similar to the manipulator assembly 302, except where described herein. In contrast to the manipulator assembly 302, the manipulator assembly 402 provides support and actuation for an elongate device drive unit 204*a* and a medical device drive unit 204*b*. Elongate device drive unit 204*a* may be coupled to a proximal portion of elongate device 202 and may be similar in construction and function as drive unit 204 described in accordance with the embodiments of FIG. 2C, with like numbers representing like parts. Medical device drive unit 204*b* may be coupled to a proximal portion of medical device 226 and may be similar in construction and function as manipulator assembly 102 of FIG. 2A, with like numbers representing like parts. Both elongate device drive unit 204*a* and medical device drive unit 204*b* may be coupled to manipulator assembly 402 which may provide actuation of mechanisms driven by both elongate device drive unit 204*a* and medical device drive unit 204*b* as well actuation for insert/retract motion of both elongate device 202 and medical device 226. Medical device drive unit 204*b* may be positioned proximally to elongate device drive unit 204*a* such that medical device 226 can be inserted into the lumen 241 of elongate device 202 providing for telescopic operation. Accordingly, medical device drive unit 204*b* may be controlled along an insertion axis A independently from elongate device drive unit 204*a*.

In some examples, the medical device 226 requires support outside of patient anatomy, e.g. proximally to reference location 408*a*. Accordingly, the elongate device 20:2 itself can provide an anti-buckling support for the medical instrument 226 during insertion of the medical device drive unit 226*b*. Similar to the proximal section of the elongate device 202 with the manipulator assembly 302, stiffening mechanism(s) in the segments 224 of the elongate device 202 may be configured in a rigid state. In various implementations, the stiffening mechanism(s) in the elongate device 202 are configured in the fully rigid state. During motion of the elongate device drive unit 204*a* and the medical device drive unit 204*b* toward the reference location 408*a*, the elongate device drive unit 204*a* configures actuation of one or more stiffening mechanisms of the elongate device 202 to transition from a rigid state to a flexible state (e.g., become more flexible). In various implementations, the stiffening mechanism(s) in the elongate device 202 are configured to transition to the fully flexible state. As the elongate device drive unit 204*a* continues to advance toward the reference location 408*a*, the segment/s 224 is/are able to collapse or compress in the flexible state as illustrated in FIG. 4A.

Initially, the reference location 408*a* may be at a first location at the patient anatomy entry. For example, upon first initiating motion of the elongate device drive unit 204*a* toward the reference location 408*a*, a distal-most segment 224 of the elongate device 202 may be transitioned to the flexible state so as to allow the distal-most segment 224 to compress. Accordingly, the reference location 408*a* may be updated to a second reference location 408*b*, which is a multiple of a compressed length of one of the segments 224. The multiple is equal to a number of the segments 224 of the elongate device 202 that have been transitioned to the flexible state. In the example shown in FIG. 4A, the reference location has been updated to a distance 456 from the base of the elongate device drive unit 204*a* which is equal to a multiple (e.g., 3 in the example shown) of the compressed length of one of the segments 224.

Figure 4B:
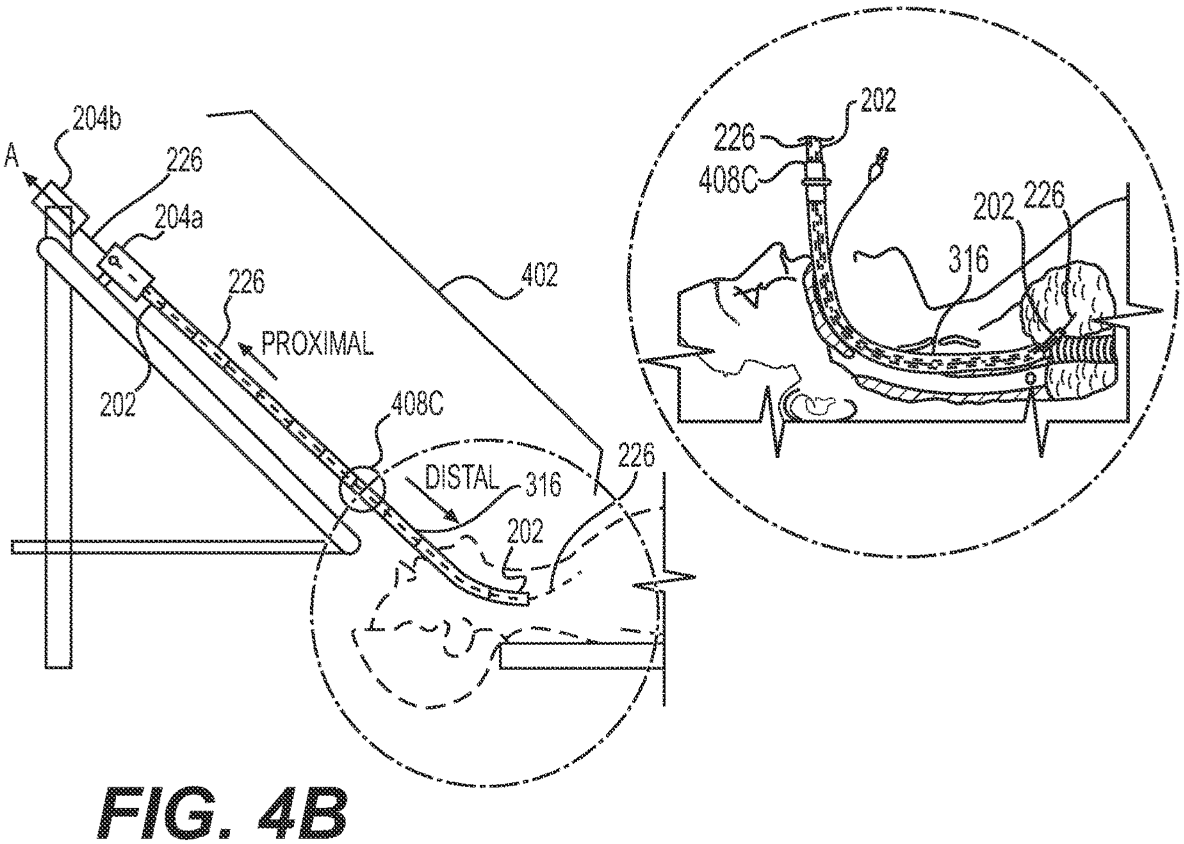
FIG. 4B is a simplified diagram of a manipulator assembly for use with a patient medical device according to some embodiments.

FIG. 4B is a simplified diagram of a manipulator assembly 402 for use with a patient medical device 316. The patient medical device 316 can be a device used to protect patient anatomy and/or facilitate introduction of minimally invasive devices such as elongate device 202 and medical device 226, into patient anatomy. Some examples of a patient medical device for access through a patient mouth include an endotracheal tube, a laryngeal mask airway, a cannula, other insertion device, etc. The patient medical device 316 can be positioned within or fixed to patient anatomy. For example, as illustrated in FIG. 4B, the patient medical device 316 may be an endotracheal tube inserted into the mouth and trachea of the patient P to help provide mechanical ventilation for the patient P and to provide a conduit for the elongate device 320 to be navigated within the lungs of the patient P to facilitate imaging, biopsy, and/or treatment. Various systems and methods related to device connectors are described in PCT/US2018/017085 (filed Feb. 6, 2018) (disclosing "Systems and methods for coupling components of a medical system"), which is incorporated by reference herein in its entirety. In other examples, not shown, the patient medical device 316 may be a cannula or an introducer used to obtain entry or access to vascular structures. In further examples, patient medical device 316 may facilitate access to other natural orifices or surgical incisions. For implementations for use with the patient medical device 316, a reference location 408*c* can be used at a location at a proximal end of the patient medical device 316 as illustrated in FIG. 4B.

In some implementations, in addition to providing anti-buckling support for elongate device 202 and/or medical device 226, the elongate device 202 may additionally replace the patient medical device 316 (such as an endotracheal tube, a laryngeal mask airway, a cannula, other insertion device, etc.). For example, for a predetermine distance past the reference location 408*c*, the drive unit 204*a* configures actuation of one or more stiffening mechanisms for performing a function of the patient medical device 316. The predetermined distance may include a predetermined length, number of segments, group of segments, or stiffening mechanisms. In some implementations, the manipulator assembly 400 may include the patient medical device 316 in addition to the elongate device 202.

In an example, the drive unit 204*a* configures actuation of one or more stiffening mechanisms for the predetermined distance to have an intermediate rigidity. The intermediate rigidity may be more flexible than the rigid state maintained in the proximal section of the elongate device 202 and more rigid than a remainder of the distal section of the elongate device 202. Such intermediate rigidity may assist with navigating through and protecting the epiglottis and vocal cords as the elongate device 202 is extended into the trachea. Additionally, the intermediate rigidity may prevent buckling of the elongate device 202 as the medical instrument 226 is passed through the epiglottis and the lung airways, as may occur when an endo-tracheal tube (ETT) is used. In some implementations, the elongate device 202 may be configured to maintain the intermediate rigidity within the trachea and configured in a more flexible state for a remainder of the distal section of the elongate device 202 within lung airways.

In some implementations, the elongate device 202 may be inserted only to a predetermined location within the patient anatomy. For example, the predetermined location may be a maximum length of the elongate device 202. In another example, the predetermined location may be where a diameter of patient anatomy is less than a predetermined diameter for safe navigation of the elongate device 202. The medical instrument 226 may pass beyond the predetermined location or another tool may pass through the working lumen 221 of the medical instrument 226 beyond the predetermined location.

In some implementations, the drive unit 204*a* configures actuation of one or more stiffening mechanisms in the flexible state for the predetermined distance during insertion of the distal end 218 of the elongate device 202 through the epiglottis and vocal cords. Subsequently, the drive unit 204*a* configures actuation of one or more stiffening mechanisms to the intermediate state for the predetermined distance. In another example, the elongate device 202 is configured to be a laryngeal mask airway (LMA). Traditional LMAs may have problems with dislodging and unsealing. The drive unit 204 configures actuation of one or more stiffening mechanisms within the elongate device 202 for facilitating insertion of the LMA. For example, one or more stiffening mechanisms within the elongate device 202 may initially be configured in a flexible state. Once inserted into a desired location, a cuff of the LMA may be inflated to anchor the LMA in place. Additionally, the drive unit may configure actuation of one or more stiffening mechanisms within the elongate device 202 to transition from the flexible state to a rigid state (e.g., become more rigid), thereby further aiding in maintaining the LMA in a desired location. A shape sensor, such as shape sensor 222, may be placed on the LMA to detect movement or dislodging of the cuff. The control system 112 may generate an alert, such as via a message displayed on display system 110 in response to detecting movement or dislodging of the LMA. Additionally, the drive unit 204 may configure actuation of one or more stiffening mechanisms within the elongate device 202 to adjust the amount of rigidity, a gradient of rigidity along a length of the elongate device 202, or otherwise shift the pose of the elongate device 454 to reseal the LMA.

Figure 5A:
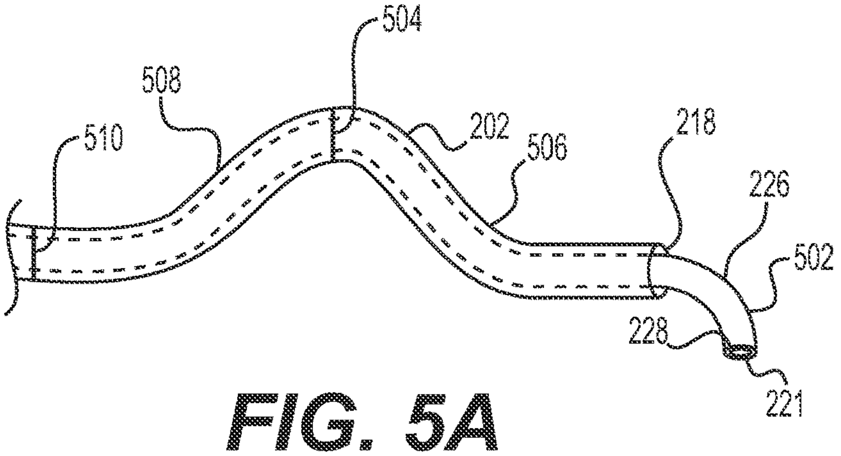
FIGS. 5A-5C are simplified diagrams showing a method of use of the variable stiffness elongate device with a medical instrument in telescopic operation for navigation of patient anatomy.
Figure 5B:
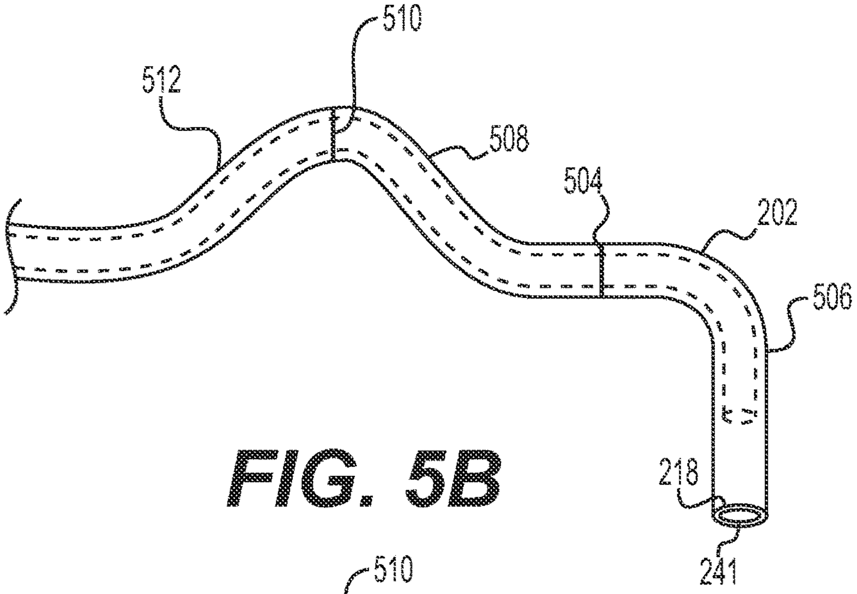
Figure 5C:
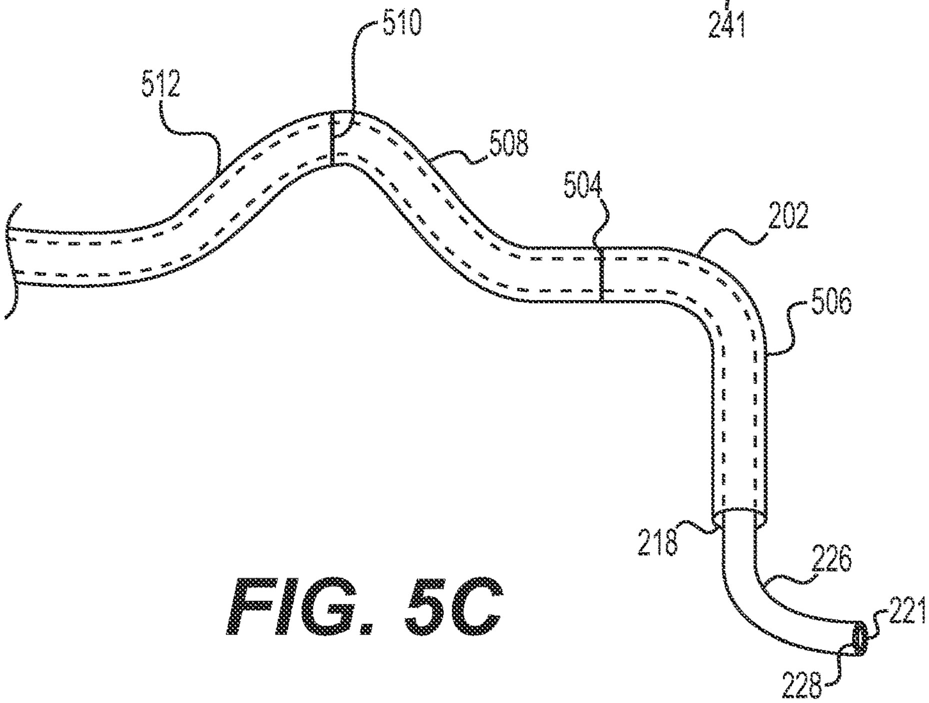

Use of a Variable Stiffness Flexible Elongate Device for Telescopic Navigation of Patient Anatomy FIGS. 5A-5C are simplified diagrams showing a method of use of the variable stiffness elongate device 202 with the medical instrument 226 in telescopic operation for navigation of patient anatomy. In the examples shown, the elongate device 202 is depicted in solid lines and the medical instrument 226 is depicted in dashed lines. As such, the medical instrument 226 is housed within the lumen 241 of the elongate device 202 and the elongate device 202 acts as a sheath for the medical instrument 226. As shown in FIG. 5A, a steerable distal end 502 of the medical instrument 226 at the distal end 228 is positioned at a location beyond the distal end 218 of the elongate device 202 for navigating a section of patient anatomy. A drive unit (e.g. drive unit 204)

configures actuation of one or more stiffening mechanisms in a first segment 506 of the elongate device 202 to be maintained in a rigid state while the steerable end 502 of the medical instrument 226 navigates the section of patient anatomy. Accordingly, the first segment 506 provides a stable platform from which to navigate the section of patient anatomy with the medical instrument 226.

The first segment 506 extends between the distal end 218 of the elongate device 202 and a proximal end 504 of the first segment 506. A second segment 508 extends between the proximal end 504 of the first segment 506 and a proximal end 510 of the second segment 508. The drive unit 204 configures actuation of one or more stiffening mechanisms in the second segment 508 of the elongate device 202 to be maintained in a rigid or flexible state. For example, the second segment 508 may have the same rigidity, be more flexible, or be more rigid than the first segment 506.

As shown in FIG. 5B, upon the steerable end 502 of the medical instrument 226 being positioned within the patient anatomy in a desired pose, the medical instrument 2:26 may be held in place. While the medical instrument 226 is held in the desired posed, the elongate device 202 is advanced past the medical instrument 226. Accordingly, the distal end 218 of the elongate device 202 is advanced beyond the steerable end 502 of the medical instrument 226. While the elongate device 202 is advanced along the steerable end 502 of the medical instrument, the drive unit 204 configures actuation of one or more stiffening mechanisms in the first segment 506 of the elongate device 202 to transition from the rigid state to a flexible state. As such, the first segment 506 is compliant for conforming to the pose of the steerable end 502 of the medical instrument 226 and advancing in a direction indicated by the steerable end 502. The elongate device 202 may be advanced a predetermined distance beyond the steerable end 502 of the medical instrument 226. In some implementations, rather than extending beyond the steerable end 502 of the medical instrument 226, the first segment 506 may be advanced along the steerable end of the medical instrument 226 until the distal end 218 of the elongate device 202 is aligned with a distal end of the steerable end 502 of the medical instrument.

Additionally, the drive unit 204 can propagate the selective stiffness of proximal segments down the length of the elongate device 202 as the elongate device 202 is inserted in anatomy. For example, as noted above with reference to FIG. 5A, the first segment 506 is configured in the rigid state at the location shown in FIG. 5A. As the elongate device is further inserted in anatomy, the first segment 506 is relaxed and the second segment 508 is selectively stiffened upon reaching a location previously occupied by the first segment 506. Likewise, as a third segment 512, positioned proximal to the proximal end 510 of the second segment 508, may conform to the pose and rigidity or flexibility previously held by the second segment 508. Thus, as the elongate device 202 is being inserted within anatomy, the elongate device 202 can be positioned in a known and controlled pose to protect anatomy instead of allowing a fully flexible device to potentially rub or press against anatomical walls.

In some examples, the actuation of one or more stiffening mechanisms along the elongate device 202 may be performed in conjunction with real-time position information, which may be displayed on display system 110 of FIG. 1 for use in the control of medical instrument system 200. In some examples, a virtual image of the elongate device 202 along with an indication of a rigidity of one or more of the segments 224 may be overlaid or integrated into the pre-operative model and the identified target areas, such as sensitive anatomy and/or tight bends may be displayed. The virtual image of the elongate device 202 may be updated based on the real-time position information obtained from tracking system 230.

For example, during a pre-procedure planning stage, a user can identify target areas of the anatomy on a pre-operative model or map, about which one or more proximate portions of the flexible body 216 may be selectively rigidized. For example, target areas of the anatomy may include anatomy which are particularly sensitive (e.g., a lung airway is near the pleura, or in a different application, the path of a flexible body 216 is near an organ). Alternatively or additionally, imaging techniques can be used to automatically identify target areas of the anatomy. Using registration of the flexible elongate device 202 with the pre-operative model and real time tracking, and the target areas of the anatomy identified during the pre-procedure planning stage, portions of the flexible body 216 which are proximate the sensitive areas of the anatomy (e.g. various segments 224 or groups of segments 224 along the length of flexible body 216) can be selectively discretely rigidized, using stiffening mechanisms to provide protection for the target area of the anatomy (e.g., sensitive anatomy) during delivery of devices through the elongate sheath 202. Accordingly, the elongate device 202 may purposefully be positioned at sensitive anatomy and one or more segments of the elongate device proximate to the sensitive anatomy may be configured in a rigid state. For example, based on the pre-operative model one of the target areas may be identified as a potential prolapse. Accordingly, rigidizing segments of the elongate device 202 proximate to the potential prolapse may be used to avoid prolapse.

Upon being positioned in a desired location beyond the steerable end 502 of the medical instrument 226, the drive unit 204 configures actuation of one or more stiffening mechanisms in the first segment 506 of the elongate device 202 to transition from a flexible state to a rigid state. As such, as shown in FIG. 5C, the steerable end 502 of the medical instrument 226 may again be advanced beyond the distal end 218 of the elongate device 202 for navigating a new section of patient anatomy.

While a particular sequence of telescopic operation of the elongate device 202 with the medical instrument 226 is described above, the pending disclosure is not so limited. In one example, the medical device 226 can be used to deliver or carry the elongate device 202 within anatomy with one or more of the segments 224 in the flexible state, the medical device 226 and elongate device 202 can both be parked within anatomy to position the distal end 218 of the flexible body 216 at a target location, then select segments 224 of the flexible body 216 may be stiffened or rigidized depending on different conditions. The medical device 226 can then disengage from the elongate device 202 and be positioned further in anatomy using the elongate device 202 as a stable platform. The various segments 224 of the flexible body 216 can be then transitioned to a flexible state and further inserted or positioned in anatomy following the shape of the medical device 226. The procedure can be repeated as desired. In another example, the medical device can be first positioned within anatomy, parked at a desired location, then the elongate device 202 can be delivered over the medical device in a flexible state, parked, and variable segments of the flexible body 216 can be rigidized. In some embodiments, various segments 224 along the flexible body 216 may switch from a rigid state to a flexible state as the flexible body navigates through anatomy depending on where the particular segments 224 are positioned within anatomy.

While described above with telescopic operation of the elongate device 202 and the medical device 226, any number of telescoping devices may be used. The telescoping devices may be any combination of steerable (e.g., robotically or manually steerable) and/or rigidizable. For example, multiple instances of the elongate device 202 and/or the medical instrument 226 may be provided.

Other methods of telescopic operation of elongate device 202 with the medical instrument 226 are contemplated. For example, while one or more of the segments 224 of the elongate device 202 proximal from the first segment 506 are maintained in a flexible state, the steerable end 502 of the medical instrument 226 may be withdrawn within the elongate device 202 to the segment maintained in the flexible state. Upon reaching the segment maintained in the flexible state, the steerable end 502 may be maneuvered within the elongate device 202 to adjust the shape or pose of the segment maintained in the flexible state. Upon the shape or pose of the segment being adjusted as desired by the steerable end 502, the segment may be transitioned to a rigid state so as to maintain the adjusted shape or pose.

Additionally, in the above examples, the elongate device 202 passively follows the path of the medical instrument 226, but in other examples, the elongate device 202 may also be steerable for navigating one or more portions of patient anatomy.

Looping

Upon introduction of catheters, endoscopes, or other such elongate devices into patient anatomy, advancement of the elongate device within patient anatomy is often complicated by looping. Looping causes the elongate device to no longer advance in a desirable 1:1 push and advance ratio when attempting to traverse patient anatomy. Therefore, looping causes additional friction on the elongate device which may eventually cause the elongate device to no longer be able to be advanced in the patient anatomy. Looping may also cause severe discomfort to patients and technical complications for a physician performing a medical procedure with the elongate device.

Moreover, in hollow cavity anatomy, the loop tends to get larger as the elongate device is advanced within the patient anatomy, further reducing the push and advance ratio. Such hollow cavity anatomy includes a voluminous cavity of patient anatomy (e.g., stomach, heart, bladder, kidney, etc.) as opposed to anatomy that forms a lumen (e.g., intestine, vein, airway, etc.). However, looping is also known to occur in anatomy that forms a lumen, such as upon advancing an elongate device through the sigmoid colon or other portions of the large intestine, small intestines, or other tortuous anatomy.

Use of a Variable Stiffness Flexible Elongate Device for Telescopic Navigation of Anatomy FIGS. 6A-8B are simplified diagrams showing particular methods of use of the variable stiffness elongate device 202 with the medical instrument 226 in telescopic operation for navigation of specific patient anatomy.

Figure 6A:
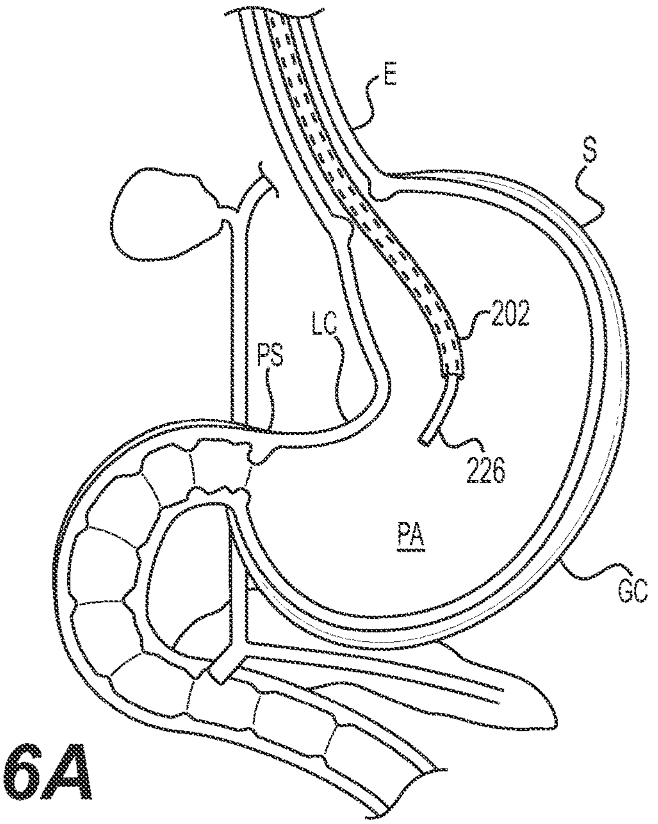
FIGS. 6A-6B are simplified diagrams showing a method of use of the variable stiffness elongate device with a medical instrument in telescopic operation for navigation of the stomach.
Figure 6B:
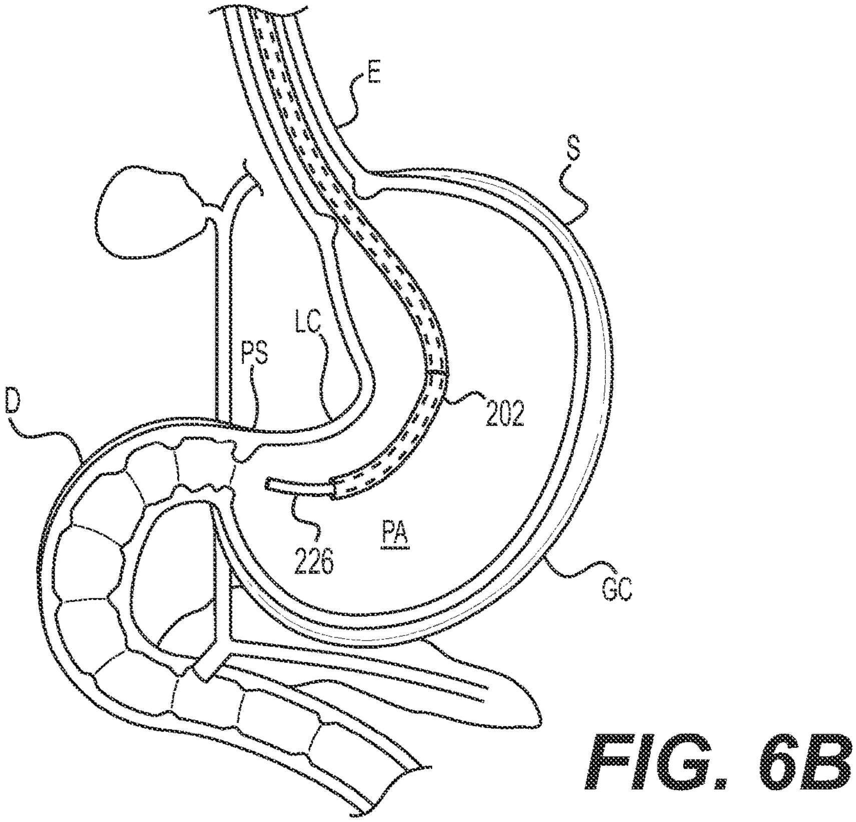

FIGS. 6A-6B are simplified diagrams showing a method of use of the variable stiffness elongate device 202 with the medical instrument 226 in telescopic operation for navigation of the stomach. Specifically, the elongate device 202 may straighten out the "J" formed by the elongate device 202 upon navigation through the stomach.

Because the stomach is so large, when navigating an instrument, such as an enteroscope or endoscope, from the esophagus, through the stomach and into the small intestine, the instrument can tend to take a long route through the stomach and extend along the greater curvature of the stomach towards the fundus as the instrument is advanced within patient anatomy. It is desirable to keep the length of travel path of the instrument as short as possible, for better articulation control of the instrument (or the instrument may not be long enough to reach a desired target). The elongate device 202 can be used to "cut the corner" within the stomach and create a shorter path towards a target anatomy.

As shown in FIG. 6A, the elongate device 202 and/or the medical instrument 226 may be passed into the stomach S from the esophagus E and follow the lesser curvature LC of the body of the stomach toward the greater curvature GC of the body of the stomach. However, as opposed to a traditional instrument, upon reaching an intermediate location between the lesser and greater curvature of the body of the stomach, proximate to the pyloric antrum PA, the elongate device 202 and/or the medical instrument 226 may remain stationary. As shown in FIG. 6B, the medical instrument 226 may be positioned at the intermediate location to point in a direction of the pyloric sphincter PS. Accordingly, the medical instrument 226 may take a "J" shape at the intermediate location within the stomach S without contacting a surface within the stomach S along the greater curvature GC.

With the medical instrument 226 positioned at the intermediate location, the drive unit 204 may actuate a stiffening mechanism in a distal segment, such as the first segment 506, of the elongate device 202 to be configured in a flexible state. In some implementations, the first segment 506 of the elongate device 202 may already be configured in a flexible state. While in the flexible state, the elongate device 202 may be advanced telescopically with the medical instrument to conform with the shape of the medical instrument 226. The elongate device 202 may continue to advance telescopically with the medical instrument until the distal end 218 of the elongate device is positioned proximate to the distal end of the medical instrument 226. In various implementations, the elongate device 202 may continue to advance until the distal end 218 of the elongate device is positioned a predetermined distance beyond the distal end of the medical instrument 226.

Upon conforming to the "J" shape of the medical instrument 226, the drive unit 204 may actuate the stiffening mechanism in the distal segment of the elongate device 202 to be configured in a rigid state. With the elongate device 202 formed in a rigid "J" shape, the medical instrument 226 may be telescopically advanced within the patient anatomy towards the pyloric sphincter PS. As opposed to pushing against the greater curvature GC of the stomach S and looping, the medical instrument 226 is pushed against the rigid "I" shaped elongate device 202. As such, the medical instrument 226 is able to advance within the patient anatomy along a shorter path through the stomach than along the greater curvature GC of the stomach S and without looping of either the elongate device 202 or the medical instrument 226.

While a particular method of telescopic navigation of the stomach S is described above, variations to the method are contemplated by this disclosure. For example, after positioning the medical instrument 226 in the "J" shape, the elongate device 202 may continue to advance telescopically with the medical instrument 226 until the distal end 218 of the elongate device 202 is positioned beyond the pyloric sphincter PS within the duodenum D. Once the distal end 218 of the elongate, device 202 is positioned within the duodenum D, a segment 224 of the elongate device 202 proximal to the distal end 218 may be rigidized to support advancement of the medical instrument 226 within the patient anatomy. For example, the drive unit 204 may actuate the stiffening mechanism in a segment 224 at the intermediate location within the stomach S to be configured in a rigid state. Thereafter, the medical instrument 226 may be advanced telescopically with the elongate device 202 toward the duodenum D. Other variations are contemplated by this disclosure.

Figure 7:
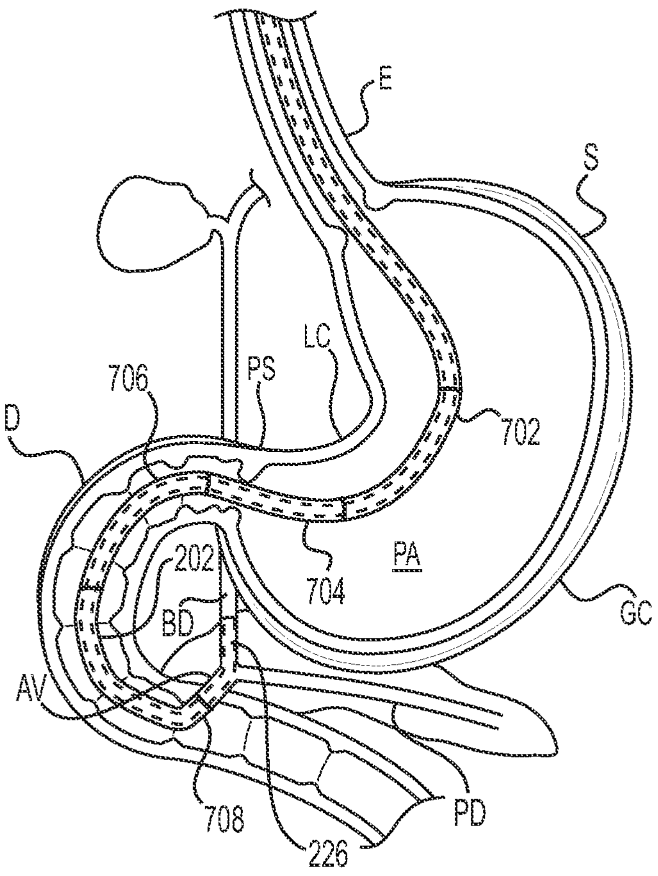
FIG. 7 is a simplified diagram showing a method of use of the variable stiffness elongate device with a medical instrument for performing an endoscopic retrograde cholangiopancreatography (ERCP).

FIG. 7 is a simplified diagram showing a method of use of the variable stiffness elongate device 202 with the medical instrument 226 for performing an endoscopic retrograde cholangiopancreatography (FRCP). ERCP may be used to diagnose and remove bile duct stones, deploy stents, perform retrograde cholangiopancreatography, or perform other therapeutic biliary or papillary interventions. Common complications from ERCP may include bleeding, perforation, pancreatitis, or cholangitis. During ERCP, the medical instrument 226 is navigated within the duodenum D through the ampulla of Vater AV (hepatopancreatic ampulla) via the major duodenal papilla and to the common bile duct BD. For some patients, cannulation of the common bile duct BD may be difficult and may result in complications due to inadvertent cannulation, irritation, and/or perforation of the main pancreatic duct PD.

Traditional techniques for aiding cannulation of the common bile duct BD include the double guidewire technique or performing a sphincterotomy, such as a transpancreatic precut sphincterotomy (TI'S) or biliary endoscopic sphincterotomy (EST). A sphincterotomy may be technically challenging and has known complications including bleeding, perforation, post-procedure and stenosis due to scarring. Therefore, such traditional techniques may increase rates or severity of complications of ERCP, such as bleeding and infection. Performing ERCP with the elongate device 202 may increase successful cannulation of the common bile duct BD by the medical instrument 226 without the added complications of the traditional techniques.

As shown in FIG. 7, a distal segment 708 of the elongate device 202, such as the first segment 506, is positioned within the duodenum D of a patient, proximate to the major duodenal papilla. For example, the distal end 218 of the elongate device 202 may be positioned past the major duodenal papilla, farther within the small intestines. In another example, the distal end 218 of the elongate device 202 may be positioned between the pyloric sphincter and the major duodenal papilla. In another example, the distal end 218 of the elongate device 202 may be positioned at the pyloric sphincter. Initially, the distal segment 708 of the elongate device 202 may be maintained in a flexible state. For example, the drive unit 204 may actuate the stiffening mechanism in the distal segment 708 to be configured in a flexible state.

With the distal segment 708 in the flexible state, the medical instrument 226 may be telescopically advanced with the elongate device 202 such that the distal end 218 of the elongate device 202 is aligned with a distal end of the medical instrument 226. For example, the medical instrument 226 may be received through the lumen 241 of the elongate device 202. The steerable distal end 502 of the medical instrument 226 is positioned in a pose in a direction of the major duodenal papilla. The pose of the medical instrument 226 can be confirmed by using endoscopic views and identifying the anatomy (e.g. the major duodenal papilla) or using navigation techniques as described below with reference to FIG. 7A. Once positioned in the pose, the distal segment 708 of the elongate device 202 may be maintained in a rigid state. For example, the drive unit 204 may actuate the stiffening mechanism in the distal segment 708 to be configured in a rigid state.

In another example, the medical instrument 226 is telescopically advanced beyond the distal end 218 of the elongate device 202 and positioned in the pose in a direction of the major duodenal papilla. For example, the steerable distal end 502 of the medical instrument 226 is positioned in the pose in a direction of the major duodenal papilla. With the distal segment 708 in the flexible state, the elongate device 202 may be advanced telescopically with the medical instrument 226 and conform to the pose held by the medical instrument 226. The elongate device 202 may be advanced telescopically with the medical instrument 226 until the distal end 218 of the elongate device 202 is aligned with a distal end of the medical instrument 226. Once conformed to the pose, the distal segment 708 of the elongate device 202 may be maintained in a rigid state. For example, the drive unit 204 may actuate the stiffening mechanism in the distal segment 708 to be configured in a rigid state.

In either case, the distal segment 708 of the elongate device 202 provides a secure platform from which the medical instrument 226 may be advanced through the ampulla of Vater AV to the common bile duct BD. In some implementations, the pose in the direction of the major duodenal papilla may be positioned at an optimal angle of approach to the major duodenal papilla to increase consistent successful cannulation of the common bile duct BD, while avoiding cannulation of the pancreatic duct. In various implementations, the shape sensor 222 on the elongate device 20:2 or a shape sensor on the medical instrument 226 may be used to verify that the medical instrument 226 and/or the elongate device 202 are positioned accurately towards the common bile duct BD. For example, the shape sensor 222 may be used to verify that the elongate device has a shape at the optimal angle of approach to the major duodenal papilla to increase consistent successful cannulation of the common bile duct BD.

In some implementations, the steerable distal end 502 of the medical instrument 226 may be used with the elongate device 202 to alter the geometry of the anatomy to make the bile duct more accessible. In some implementations, once the distal segment 708 is configured in a rigid state in the pose, a sphincterotomy may be performed with increased precision with the aid of the stable platform provided by the rigid distal segment 708.

Additionally shown in FIG. 7, various ones of the segments of the elongate device 202 may be configured in different states. For example, as described above, a first segment 702 of the elongate device 202 may be positioned at the intermediate location between the lesser curvature LC and the greater curvature GC of the stomach proximate to the pyloric antrum PA. Accordingly, the first segment 702 may be maintained in a rigid state to prevent the medical instrument 226 or the elongate device 202 from looping within the stomach S.

Likewise, a second segment 704 of the elongate device 202 may be positioned at a location passing through the pyloric sphincter PS. As such, the second segment 704 may be maintained in a flexible state so as to conform to muscular movements caused by the pyloric sphincter PS. A third segment 706 of the elongate device 202 may be positioned at an initial curve of the duodenum. The third segment 706 may be configured in a rigid state to again prevent looping of the medical instrument 226 or the elongate device 202 within the duodenum.

While particular segments are described above as being configured in a particular state, more or fewer segments may be present on the elongate device 202 and alternative configurations may be used as described in the above examples. For example, the second segment 704 may be configured in some implementations to be in a rigid state to resist muscular movement caused by the pyloric sphincter PS. Regardless of the particular number, location, or configuration of the segments, it is clear that different segments at different locations along the elongate device 202 may be configured in different states, as needed or desired depending on the anatomy proximate to each of the segments.

In another example, the elongate device 202 may be registered to a pre-operative model of a patient anatomy. Using localization sensors, such as a shape sensor and/or position sensor on the elongate device 202 or the medical instrument 226, a real time position of the elongate device 202 within the model of the patient anatomy may be determined. The elongate device 202 may be positioned based on a rendering, such as on display system 110, of the model of the patient anatomy with the elongate device 202 shown therein.

Figure 7A:
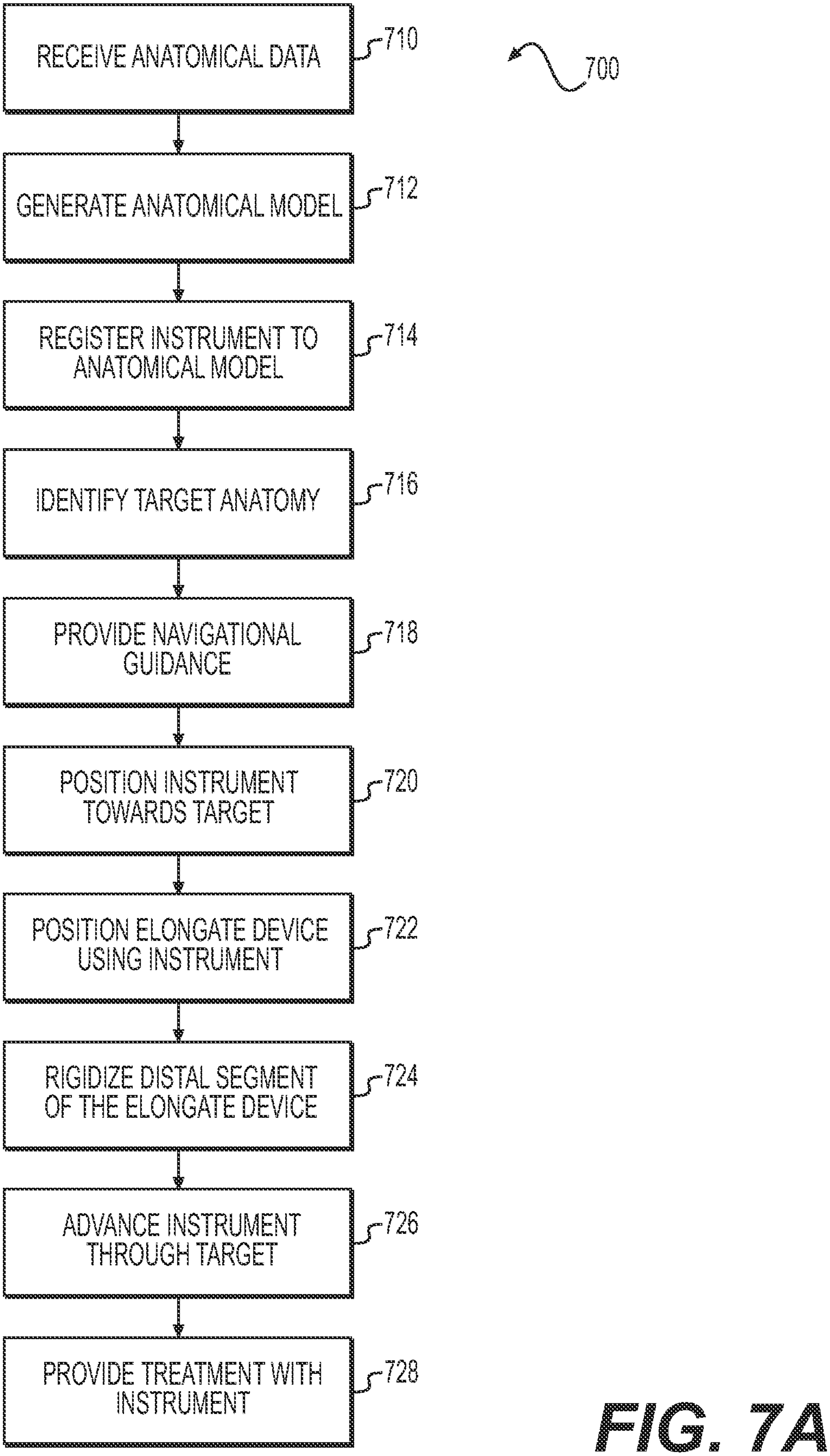
FIG. 7A is a simplified flow diagram showing a method of use of the variable stiffness elongate device with the medical instrument for navigating through a target anatomy.

FIG. 7A is a simplified diagram showing a method 700 of use of the variable stiffness elongate device 202 with the medical instrument 226 for navigating through a target anatomy. At 710, the control system 112 receives anatomical data of a patient, such as pre-operative imaging data. At 712, the control system 112 uses the anatomical data to generate an anatomical model of the patient. At 714, the medical instrument 226 is registered to the anatomical model to show a real time position of the medical instrument 226 within the anatomical model, such as on a rendering on display system 110. At 716, a target anatomy is identified on the anatomical model. Following the example above, the target anatomy may be the common bile duct BD. At 718, navigational guidance may be provided on the display system 110 to direct the medical instrument 226 to the target anatomy, such as to the duodenum D of a patient, proximate to the major duodenal papilla. At 720, the medical instrument 226 is positioned toward the target anatomy. For example, the medical instrument 226 may be positioned in a pose in a direction of the major duodenal papilla at an angle of approach to the major duodenal papilla to increase consistent successful cannulation of the common bile duct BD, while avoiding cannulation of the pancreatic duct.

At 722, the elongate device 202 is positioned within the patient anatomy towards the target anatomy using the medical instrument 226. For example, the elongate device 202 may, be advanced telescopically with the medical instrument 226 and conform to the pose held by the medical instrument 226. As such, the elongate device 202 is positioned in the pose in a direction of the major duodenal papilla at the angle of approach to the major duodenal papilla to increase consistent successful cannulation of the common bile duct BD, while avoiding cannulation of the pancreatic duct. At 724, one or more distal segments of the elongate device 202 is rigidized to maintain the elongate device 202 in the pose. For example, the drive unit 204 may actuate the stiffening mechanism in the one or more distal segments to be configured in a rigid state.

At 726, the medical instrument 226 or another medical tool may be advanced through the lumen 241 of the elongate device 202 and on through the target anatomy. For example, the medical instrument 226 or other tool may be advanced through the ampulla of Vater AV to the common bile duct BD. At 728, the medical instrument 226 or other tool may optionally perform a therapeutic or diagnostic procedure.

Figure 8A:
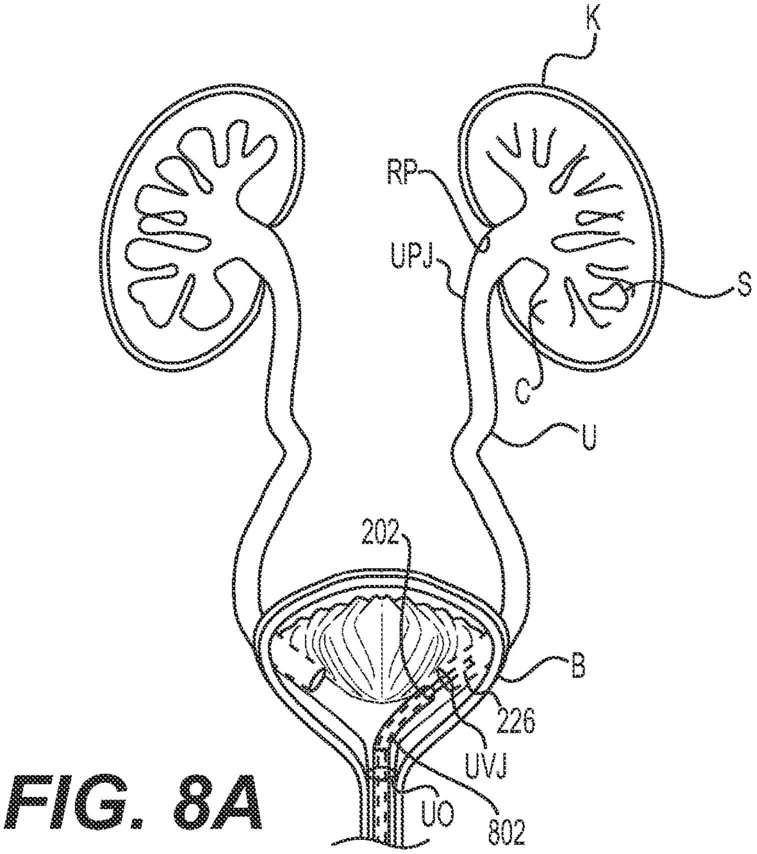
FIGS. 8A-8B are simplified diagrams showing a method of use of the variable stiffness elongate device with the medical instrument for performing a ureteroscopy.
Figure 8B:
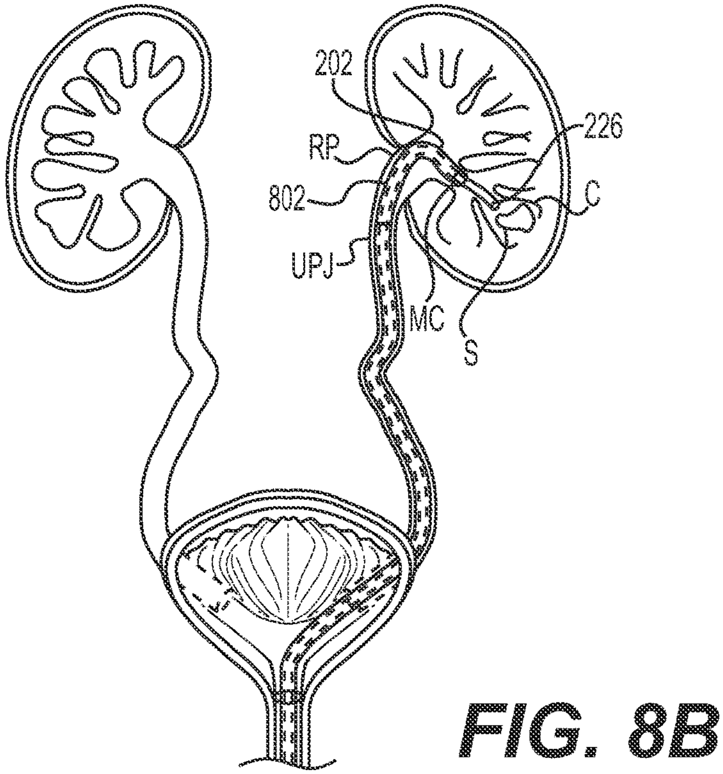

FIGS. 8A-8B are simplified diagrams showing a method of use of the variable stiffness elongate device 202 with the medical instrument 226 for performing a ureteroscopy. A ureteroscopy is used to diagnose and treat a variety of problems in the urinary tract, such as kidney stones S. However, upon navigating an elongate device, such as a cystoscope, past the internal urethral orifice UO into the bladder B, it may be difficult to cannulate a ureter U at the ureterovesical junction UVJ. Additionally, navigation of an elongate device through the ureteropelvic junction UPJ and the renal pelvis RP may be difficult, particularly for the treatment of kidney stones S located in a calyx C in a lower portion of the kidney K.

As shown in FIG. 8A, a distal segment 802 of the elongate device 202, such as the first segment 506, is inserted into the bladder B of a patient past the internal urethral orifice UO and positioned proximate to a ureterovesical junction UVJ. For example, the distal end 218 of the elongate device 202 may be positioned past the ureterovesical junction UVJ, farther within the bladder B. In another example, the distal end 218 of the elongate device 202 may be positioned between internal urethral orifice UO and the ureterovesical junction UVJ. In another example, the distal end 218 of the elongate device 202 may be positioned at the ureterovesical junction UVJ. Initially, the distal segment 802 of the elongate device 202 may be maintained in a flexible state. For example, the drive unit 204 may actuate the stiffening mechanism in the distal segment 802 to be configured in a flexible state.

With the distal segment 802 in the flexible state, the medical instrument 226 may be telescopically advanced with the elongate device 202 such that the distal end 218 of the elongate device 202 is aligned with a distal end of the medical instrument 226. For example, the medical instrument 2:26 may be received through the lumen 241 of the elongate device 202, The steerable distal end 502 of the medical instrument is positioned in a pose in a direction of the ureterovesical junction UVJ. Once positioned in the pose, the distal segment 802 of the elongate device 202 may be maintained in a rigid state. For example, the drive unit 204 may actuate the stiffening mechanism in the distal segment 802 to be configured in a rigid state.

In another example, the medical instrument 226 is telescopically advanced beyond the distal end 218 of the elongate device 202 and positioned in the pose in a direction of the ureterovesical junction UVJ. For example, the steerable distal end 502 of the medical instrument is positioned in the pose in a direction of the ureterovesical junction UVJ, With the distal segment 802 in the flexible state, the elongate device 202 may be advanced telescopically with the medical instrument 226 and conform to the pose held by the medical instrument 226. The elongate device 20:2 may be advanced telescopically with the medical instrument 226 until the distal end 218 of the elongate device 202 is aligned with a distal end of the medical instrument 226. Once conformed to the pose, the distal segment 802 of the elongate device 202 may be maintained in a rigid state. For example, the drive unit 204 may actuate the stiffening mechanism in the distal segment 802 to be configured in a rigid state.

In either case, the distal segment 802 of the elongate device 202 provides a secure platform from which the medical instrument 226 may be advanced through the ureterovesical junction UVJ to cannulate the ureter U. In various implementations, the shape sensor 222 on the elongate device 202 or a shape sensor on the medical instrument 226 may be used to verify that the medical instrument 226 and/or the elongate device 202 are positioned accurately towards the ureterovesical junction UVJ.

In some implementations, the steerable distal end 502 of the medical instrument 226 may be used with the elongate device 202 to alter the geometry of the anatomy to make the ureterovesical junction UVJ more accessible.

As shown in FIG. 8B, the distal segment 802 of the elongate device 202 is inserted through the ureteropelvic junction UPJ into the renal pelvis RP of a patient and positioned proximate to a target major calyx MC in a lower portion of the kidney K. For example, the distal end 218 of the elongate device 202 may be positioned between the ureteropelvic junction UN and the target major calyx MC. In another example, the distal end 218 of the elongate device 202 may be positioned at a major calyx MC above the target major calyx MC. Initially, the distal segment 802 of the elongate device 202 may be maintained in a flexible state. For example, the drive unit 204 may actuate the stiffening mechanism in the distal segment 802 to be configured in a flexible state.

With the distal segment 802 in the flexible state, the medical instrument 226 may be telescopically advanced with the elongate device 202 such that the distal end 218 of the elongate device 202 is aligned with a distal end of the medical instrument 226. For example, the medical instrument 226 may be received through the lumen 241 of the elongate device 202. The steerable distal end 502 of the medical instrument is positioned in a pose in a direction of the target major calyx MC. Once positioned in the pose, the distal segment 802 of the elongate device 202 may be maintained in a rigid state. For example, the drive unit 204 may actuate the stiffening mechanism in the distal segment 802 to be configured in a rigid state.

In another example, the medical instrument 226 is telescopically advanced beyond the distal end 218 of the elongate device 202 and positioned in the pose in a direction of the target major calyx MC. For example, the steerable distal end 502 of the medical instrument is positioned in the pose in a direction of the target major calyx MC. With the distal segment 802 in the flexible state, the elongate device 202 may be advanced telescopically with the medical instrument 226 and conform to the pose held by the medical instrument 226. The elongate device 202 may be advanced telescopically with the medical instrument 226 until the distal end 218 of the elongate device 202 is aligned with a distal end of the medical instrument 226. Once conformed to the pose, the distal segment 802 of the elongate device 202 may be maintained in a rigid state. For example, the drive unit 204 may actuate the stiffening mechanism in the distal segment 802 to be configured in a rigid state.

In either case, the distal segment 802 of the elongate device 202 provides a secure platform from which the medical instrument 226 may be advanced through the target major calyx MC to a desired minor calyx for treatment of kidney stones S. In various implementations, the shape sensor 222 on the elongate device 202 or a shape sensor on the medical instrument 226 may be used to verify that the medical instrument 226 and/or the elongate device 202 are positioned accurately towards the target major calyx MC.

Figure 9:
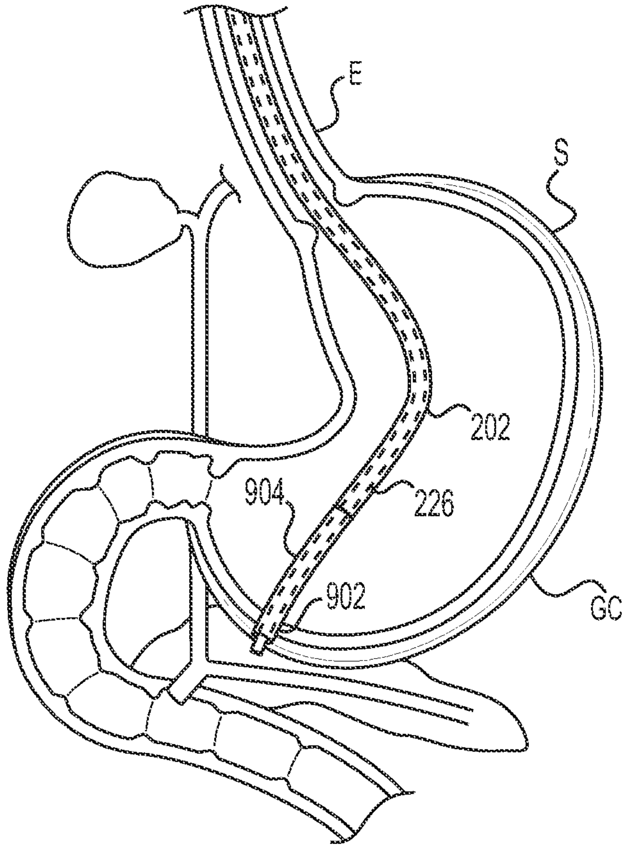
FIG. 9 is a simplified diagram showing a method of use of the variable stiffness elongate device as an anchor during a transgastric necrosectomy.
Figure 10:
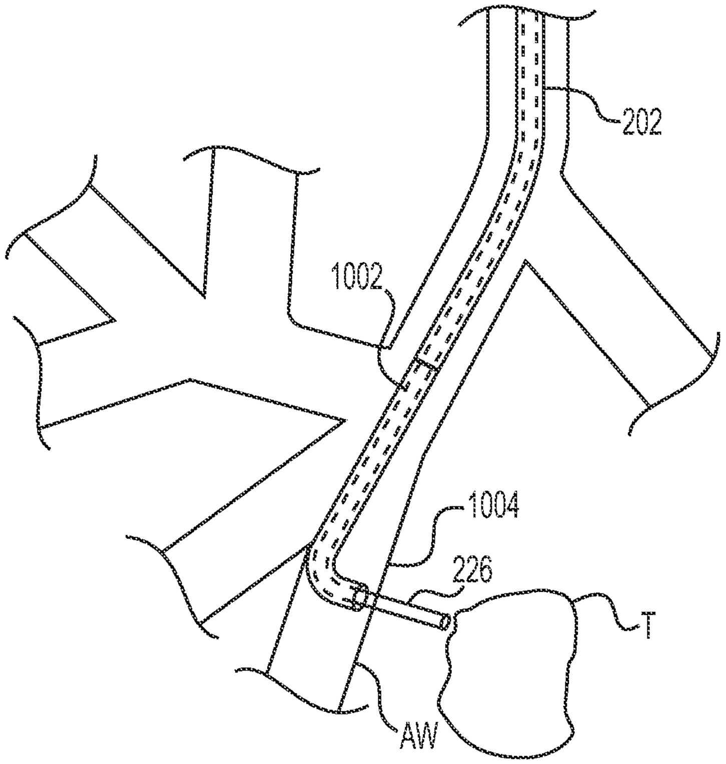
FIG. 10 is a simplified diagram showing a method of use of the variable stiffness elongate device as an anchor during delivery of an ablation probe through an airway.
Figure 11:
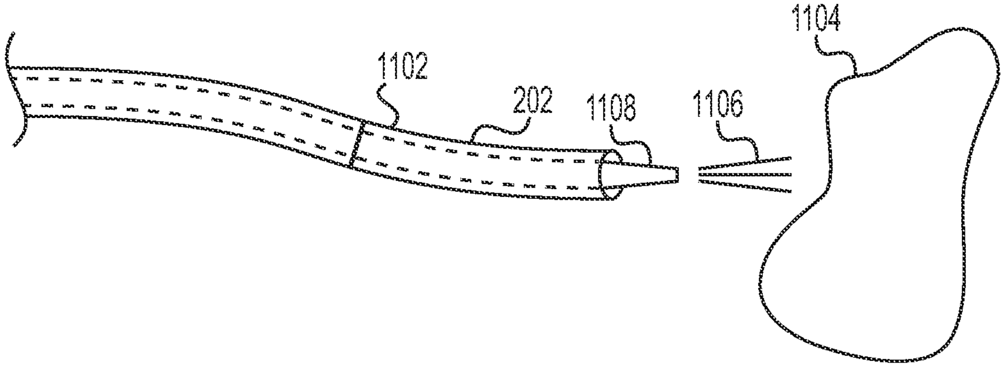
FIG. 11 is a simplified diagram showing a method of use of the variable stiffness elongate device as an anchor during delivery of high velocity fluids.

Use of a Variable Stiffness Flexible Elongate Device as an Anchor for Medical Procedures FIGS. 9-11 are simplified diagrams showing particular methods of use of the variable stiffness elongate device 202 with the medical instrument 226 an anchor in patient anatomy while performing medical procedures with the medical instrument 226.

FIG. 9 is a simplified diagram showing a method of use of the variable stiffness elongate device 20:2 as an anchor during a transgastric necrosectomy or endoscopic cystogastrostomy. Such procedures include accessing the pancreas via a small full-thickness gastrostomy (stomach incision). Using the access gained through the stomach, the transgastric necrosectomy facilitates removal of necrotic portions of the pancreas or otherwise removes or breaks up cysts or other target tissue. The incision through the stomach may be performed with the medical instrument 226 or another tool, such as a needle knife or other cutting tool, supplied through the working lumen 221 of the medical instrument 226 or the lumen 241 of the elongate device 202. The elongate device 202 may be used as an anchor to stabilize the cutting tool during the gastrostomy.

As shown in FIG. 9, a distal segment 904 of the elongate device 202, such as the first segment 506, is inserted into the stomach S of a patient via the esophagus E and positioned proximate to a target location 902 along the greater curvature GC of the body of the stomach S. For example, the distal end 218 of the elongate device 202 may be positioned in the pyloric antrum PA. In another example, the distal end 218 of the elongate device 202 may be positioned at the target location 902. Initially, the distal segment 904 of the elongate device 202 may be maintained in a flexible state. For example, the drive unit 204 may actuate the stiffening mechanism in the distal segment 904 to be configured in a flexible state.

With the distal segment 904 in the flexible state, the medical instrument 226 may be telescopically advanced with the elongate device 202 such that the distal end 218 of the elongate device 202 is aligned with a distal end of the medical instrument 226. For example, the medical instrument 226 may be received through the lumen 241 of the elongate device 202. The steerable distal end 502 of the medical instrument is positioned in a pose in a direction of the target location 902. Once positioned in the pose, the distal segment 904 of the elongate device 202 may be maintained in a rigid state. For example, the drive unit 204 may actuate the stiffening mechanism in the distal segment 904 to be configured in a rigid state.

In another example, the medical instrument 226 is telescopically advanced beyond the distal end 218 of the elongate device 202 and positioned in the pose in a direction of the target location 902. For example, the steerable distal end 502 of the medical instrument is positioned in the pose in a direction of the target location 902. With the distal segment 904 in the flexible state, the elongate device 202 may be advanced telescopically with the medical instrument 226 and conform to the pose held by the medical instrument 226. The elongate device 202 may be advanced telescopically with the medical instrument 226 until the distal end 218 of the elongate device 202 is aligned with a distal end of the medical instrument 226. Once conformed to the pose, the distal segment 904 of the elongate device 202 may be maintained in a rigid state. For example, the drive unit 204 may actuate the stiffening mechanism in the distal segment 904 to be configured in a rigid state.

In either case, the distal segment 904 of the elongate device 202 provides a secure platform from which the medical instrument 2:26 may perform the gastrostomy. In various implementations, the shape sensor 222 on the elongate device 202 or a shape sensor on the medical instrument 226 may be used to verify that the medical instrument 226 and/or the elongate device 202 are positioned accurately in a desired pose towards target location 902. The desired pose may provide an optimized angle of approach to cysts, necrotic tissue, or other target tissue. Once the gastrostomy has been completed, the elongate device 202 may be advanced through the incision in the desired pose to provide the medical instrument 226 with access to the pancreas at the optimized angle of approach.

In some implementations, the steerable distal end 502 of the medical instrument 226 may be used with the elongate device 202 to alter the geometry of the anatomy to make the target location 902 more accessible. For example, rugal folds of the stomach or haustra of the colon may be flattened out, as described in more detail below with reference to FIGS. 15A-15D.

While the example of FIG. 9 is described above with respect to performing a transgastric necrosectomy, other transgastric procedures may similarly be performed used the same techniques. For example, the variable stiffness elongate device 202 may similarly provide a stable platform for performing a cholecystectomy or cystogastrostomy via a gastrostomy.

FIG. 10 is a simplified diagram showing a method of use of the variable stiffness elongate device 202 as an anchor during delivery of an ablation probe to an anatomical target, e.g. to a tumor within a lung through an airway wall AW. In alternative embodiments, other anatomical targets could be provided. The variable stillness elongate device 202 provides a simple mechanism to both deploy and collapse an anchor via the ability to configure one or more segments of the elongate device 202 in a rigid or flexible configuration. Moreover, configuring a distal segment 1002 of the elongate device 202 in a rigid state provides more structure and support for puncturing the airway wall AW while at the same time allows proximal segments of the elongate device 202 to remain configured in a flexible state to be able to move with anatomy, as described in more detail below with reference to FIGS. 16A-17C. The ablation probe may be integrated with medical instrument 226, may be provided through a working lumen of the medical instrument 226, or supplied through the lumen 241 of the elongate device 202. Therefore, while the distal segment of the elongate device 202 provides rigid structure to aide in puncturing the airway AW and puncturing tumor T, once within the tumor T, the ablation probe is free to move with anatomy—and thus move with the tumor as the tumor shifts.

As shown in FIG. 10, the distal segment 1002 of the elongate device 202, such as the first segment 506, is inserted into an airway of a patient and positioned proximate to a target location 1004 adjacent to the tumor T. The elongate device 202, can be inserted in a flexible state. The distal segment 1002 of the elongate device may then be positioned proximate to the target location 1004 by telescopically following a steerable catheter, such as medical instrument 226, or working in concert with the steerable catheter, as described above. In other embodiments, the elongate device 202 may be steerable and may be positioned proximate the target using steering mechanisms as previously described, Initially, the elongate device 202 may be maintained in a flexible state. For example, the drive unit 204 may actuate the stiffening mechanism in the distal segment 904 to be configured in a flexible state.

With the distal segment 1002 in the flexible state, the medical instrument 226 may be telescopically advanced with the elongate device 202 such that the distal end 218 of the elongate device 202 is aligned with a distal end of the medical instrument 226. For example, the medical instrument 226 may be received through the lumen 241 of the elongate device 202. The steerable distal end 502 of the medical instrument 226 is positioned in a pose in a direction of the target location 1004. Once positioned in the pose, the distal segment 1002 of the elongate device 202 may be maintained in a rigid state. For example, the drive unit 204 may actuate the stiffening mechanism in the distal segment 1004 to be configured in a rigid state.

In another example, the medical instrument 226 or another device (e.g., therapeutic or diagnostic probe, needle knife, ablation probe etc.) is telescopically advanced through the lumen 241 beyond the distal end 218 of the elongate device 202 and positioned in the pose in a direction of the target location 1004. For example, the steerable distal end 502 of the medical instrument is positioned in the pose in a direction of the target location 1004. With the distal segment 1002 in the flexible state, the elongate device 202 may be advanced telescopically with the medical instrument 226 and conform to the pose held by the medical instrument 226. The elongate device 202 may be advanced telescopically with the medical instrument 226 until the distal end 218 of the elongate device 202 is aligned with a distal end of the medical instrument 226. Once conformed to the pose, the distal segment 1002 of the elongate device 202 may be maintained in a rigid state. For example, the drive unit 204 may actuate the stiffening mechanism in the distal segment 1002 to be configured in a rigid state.

In a further example, when the elongate device 202 is itself steerable, the elongate device 202 is positioned in the pose in a direction of the target location 1004. For example, the distal segment 1002 may be maintained in the flexible state while one or more control wires or other control mechanisms on the elongate device 202 position the elongate device in the pose. Once positioned in the pose, the distal segment 1002 of the elongate device 202 may be maintained in a rigid state. For example, the drive unit 204 may actuate the stiffening mechanism in the distal segment 1002 to be configured in a rigid state.

In a still further example, a wire shaped into a desired shape is inserted through the lumen 241 of the elongate device 202 so that the elongate device 202 forms an anchored shape at the distal segment 100:2. Once conformed to the desired shape, the distal segment. 1002 of the elongate device 20:2 which has formed into the desired shape may be actuated into a rigid state. For example, the drive unit 204 may actuate the stiffening mechanism in the distal segment 1002 to be configured in a rigid state. In some implementations, the elongate device 202 may also comprise an expandable sheath at the distal segment 1002. Once conformed to the desired shape and configured in the rigid state, the expandable sheath may be expanded to form a full anchor to lock into the anatomy.

In any case, the distal segment 1002 of the elongate device 20:2 provides a secure platform from which a therapeutic or diagnostic probe or other tool (e.g., ablation probe) may puncture the airway AW and the tumor T. In various implementations, the shape sensor 222 on the elongate device 202 or a shape sensor on the medical instrument 226 may be used to verify that the medical instrument 226 and or the elongate device 202 are positioned accurately in a desired pose towards target location 1004. The desired pose may provide an optimized angle of approach to the tumor T. Upon completion of the therapeutic procedure, the distal segment 1002 of the elongate device 202 is configured in a flexible state to facilitate removal of the elongate device 202 from the airway AW.

Figure 10A:
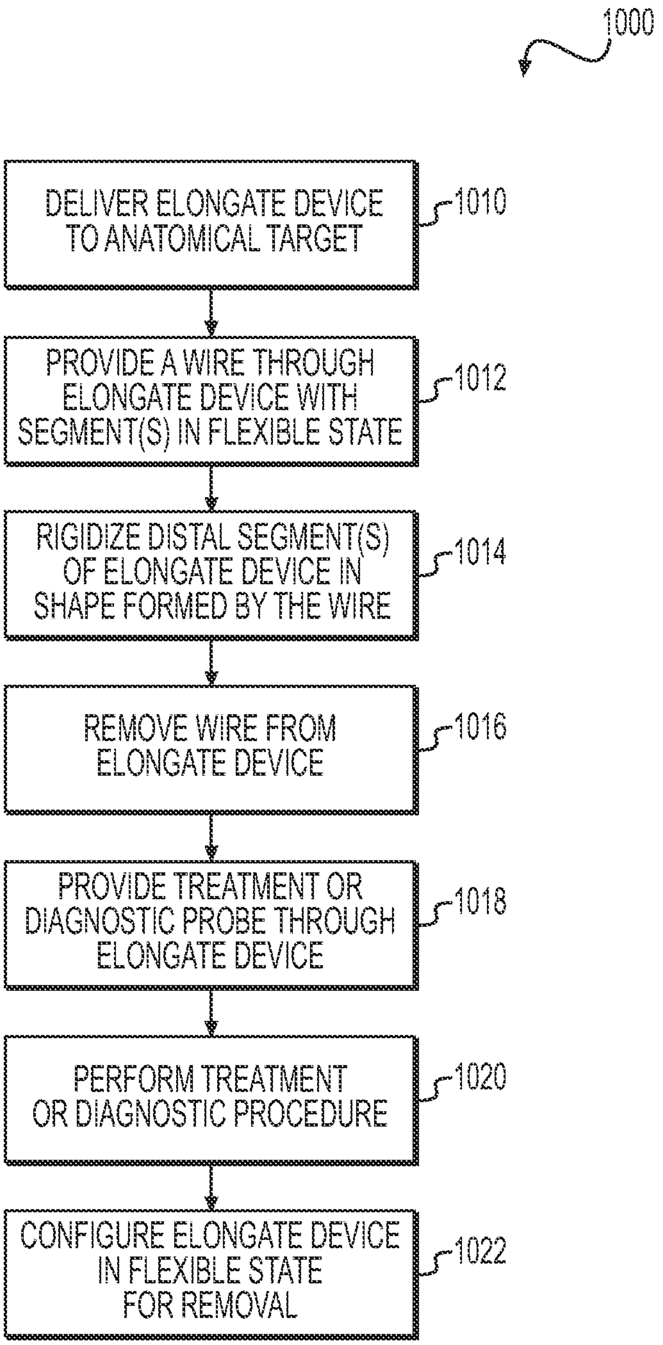
FIG. 10A is a simplified flow diagram showing a method of use of the variable stiffness elongate device for forming an anchor in patient anatomy for performance diagnostic or therapeutic procedures.

FIG. 10A is a simplified diagram showing a method 1000 of use of the variable stiffness elongate device 202 for forming an anchor in patient anatomy for performance diagnostic or therapeutic procedures. At 1010, the elongate device 202 is delivered to an anatomical target. Following the example above, the anatomical target may be in an airway AW of a patient adjacent to a tumor T. When positioned at the anatomical target, one or more distal segments of the elongate device 202 may be configured in a flexible state. At 1012, a wire shaped into a desired shape is inserted through the lumen 241 of the elongate device 202 so that the one or more distal segments of the elongate device 202 forms a desired shape. For example, the desired shape may anchor the elongate device 202 into patient anatomy at the anatomical target. At 1014, once conformed to the desired shape, the one or more distal segments of the elongate device 202 may be maintained in a rigid state. For example, the drive unit 204 may actuate the stiffening mechanism in the one or more distal segments to be configured in a rigid state to maintain the desired shape within the anatomical target.

At 1016, the wire may be withdrawn from the elongate device 202 while maintaining the one or more distal segments of the elongate device in the rigid state. At 1018, a therapeutic or diagnostic probe or other medical instrument is inserted through the lumen 241 of the elongate device. At 1020, a diagnostic or therapeutic procedure is performed using the probe with the elongate device 202 rigidly positioned in the desired shape at the anatomical target. In various examples, the probe may extend beyond the distal end 218 of the elongate device 202 during the procedure. The probe may be removed from the elongate device upon completion of the procedure. At 1022, upon completion of the procedure, the one or more distal segments of the elongate device 202 are maintained in a flexible state to facilitate removal of the elongate device 202 from the patient anatomy. For example, the drive unit 204 may actuate the stiffening mechanism in the one or more distal segments to be configured in a flexible state to remove the elongate device 202. Upon being configured in the flexible state, the elongate device 202 may no longer maintain the desired shape within the anatomical target.

FIG. 11 is a simplified diagram showing a method of use of the variable stiffness elongate device 202 as an anchor during delivery of high velocity fluids. Delivery of high velocity fluids using flexible devices is difficult because the velocity of the fluid forces the flexible device to deform and lose its desired shape. Procedures that use delivery of high velocity fluids include, but are not limited to, providing sub-mucosal lift during sub mucosal dissection, cataract treatment, breaking up a bone in the sinus, breaking bone spurs to treat nerve impingement, treatment of benign hyperplastic hyperplasia (BPH) in the prostate, among others. High velocity fluids may be delivered via an infusion catheter, or other fluidic delivery device.

As shown in FIG. 11, a distal segment 1102 of the elongate device 202, such as the first segment 506, is inserted into anatomy of a patient and positioned proximate to a target location 1104 for treatment by high velocity fluids. The distal segment 1102 of the elongate device may be positioned proximate to the target location 1104 by telescopically following a steerable catheter, such as medical instrument 226, or working in concert with the steerable catheter, as described above. Initially, the distal segment 1102 of the elongate device 202 may be maintained in a flexible state. For example, the drive unit 204 may actuate the stiffening mechanism in the distal segment 904 to be configured in a flexible state.

With the distal segment 1002 in the flexible state, the medical instrument 226 may be telescopically advanced with the elongate device 202 such that the distal end 218 of the elongate device 202 is aligned with a distal end of the medical instrument 226. For example, the medical instrument 226 may be received through the lumen 241 of the elongate device 202. The steerable distal end 502 of the medical instrument 226 is positioned in a pose in a direction of the target location 1104. Once positioned in the pose, the distal segment 1102 of the elongate device 202 may be maintained in a rigid state. For example, the drive unit 204 may actuate the stiffening mechanism in the distal segment 1104 to be configured in a rigid state.

In another example, the medical instrument 226 is telescopically advanced beyond the distal end 218 of the elongate device 202 and positioned in the pose in a direction of the target location 1104. For example, the steerable distal end 502 of the medical instrument is positioned in the pose in a direction of the target location 1104. With the distal segment 1102 in the flexible state, the elongate device 202 may be advanced telescopically with the medical instrument 226 and conform to the pose held by the medical instrument 226. The elongate device 202 may be advanced telescopically with the medical instrument 226 until the distal end 218 of the elongate device 202 is aligned with a distal end of the medical instrument 226. Once conformed to the pose, the distal segment 1102 of the elongate device 202 may be maintained in a rigid state. For example, the drive unit 204 may actuate the stiffening mechanism in the distal segment 1102 to be configured in a rigid state. Other methods of positioning the distal segment 1102 of the elongate device in the pose in a direction of the target location 1104 are contemplated by this disclosure.

In various implementations, in addition to configuring the distal segment 1102 in a rigid state, one or more segments 224 of the elongate device 202 may additionally be configured in a rigid state. In any case, the distal segment 1102 of the elongate device 202 provides a secure platform from which high velocity fluids 1106 may be provided from a high velocity fluid delivery tool 1108. In various implementations, the shape sensor 222 on the elongate device 202 or a shape sensor on the medical instrument 226 may be used to verify that the medical instrument 226 and/or the elongate device 202 are positioned accurately in a desired pose towards target location 1104.

Figure 12A:
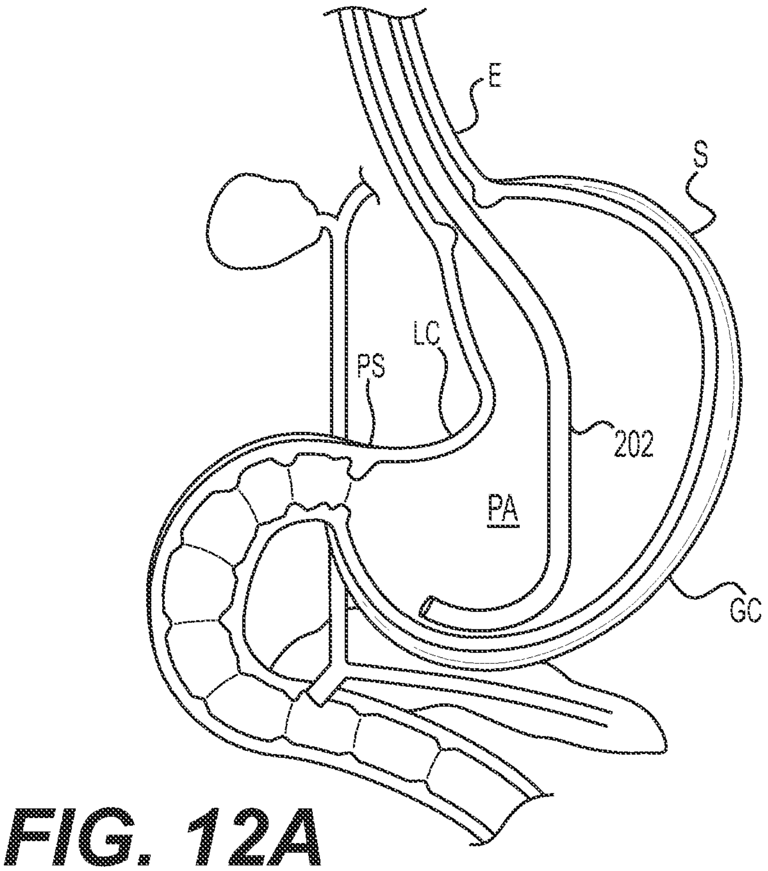
FIGS. 12A-12B are simplified diagrams showing a method of use of the variable stiffness elongate device to optimally navigate through the stomach of a patient.
Figure 12B:
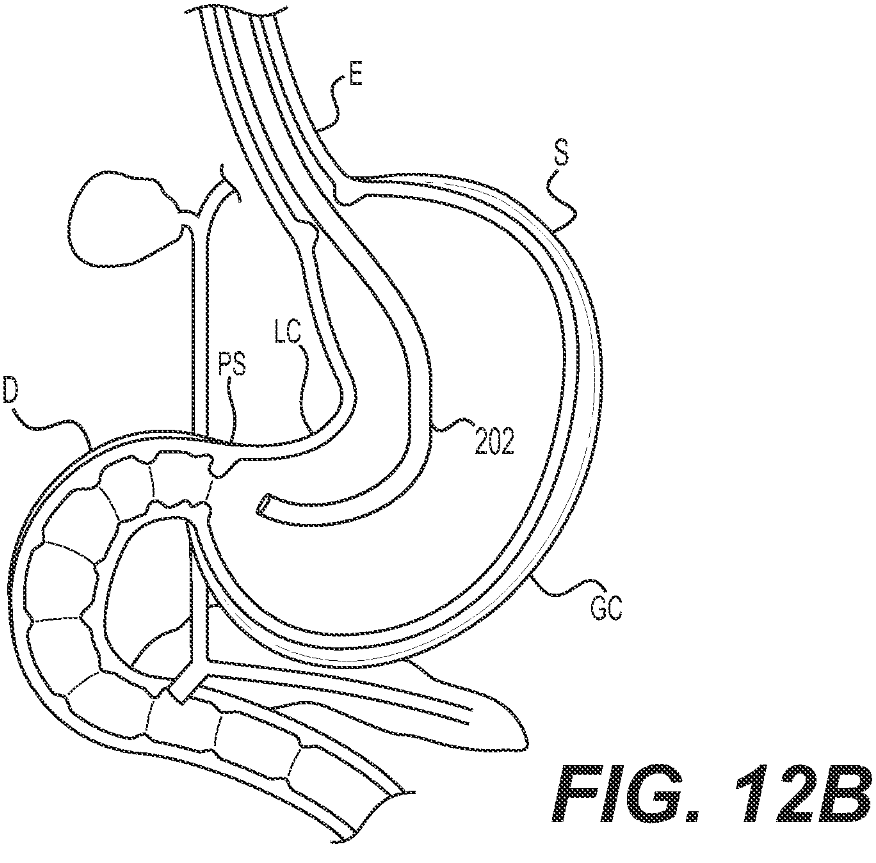

Use of a Variable Stiffness Flexible Elongate Device for Improved Navigation of Anatomy In the examples provided above, the elongate device 202 is navigated telescopically with the medical instrument 226 for navigating patient anatomy. FIGS. 12A-13B provide examples of using the variable stiffness elongate device 202 itself to improve navigation of patient anatomy. In each of the examples described below, the elongate device 202 leverages the natural shape of a patient's anatomy to conform the elongate device 202 to a desired shape. Once positioned in the desired shape, a distal segment of the elongate device 202 is configured in a rigid state to maintain the desired shape and a proximal end of the elongate device 202 can be withdrawn, e.g., drive unit 204*a* ban be translated in the retraction direction, from the patient anatomy to align the flexible body 216 of the elongate device 202 with a desired, shorter path of travel for the medical instrument 226 or other tool inserted through the lumen 241, FIGS. 12A-12B are simplified diagrams showing a method of use of the variable stiffness elongate device 202 to optimally navigate through the stomach of a patient. As shown in FIG. 12A, the elongate device 202 is configured in a flexible state and passed into the stomach S from the esophagus E and the distal end 218 follows along with the shape of the greater curvature GC of the body of the stomach S. Therefore, the distal end 218 of the elongate device 202 conforms to a naturally hooked or "1" shape. With the elongate device 202 positioned in a desired shape, the drive unit 204 may actuate a stiffening mechanism in a distal segment, such as the first segment 506, of the elongate device 202 to be configured in a rigid state to maintain the desired shape, e.g. hooked shape, "J" shape, or anchor shape. In some implementations, one or more additional segments proximal to the distal segment may additionally be configured in the rigid state. In various implementations, the shape sensor 222 on the elongate device 202 may be used to verify that the elongate device 202 is positioned in the desired shape along the greater curvature GC of the stomach S. Based on feedback from the shape sensor 222 an additional length of the elongate device 202 may be inserted into the stomach S or a length of the elongate device 202 may be retracted from the stomach S, by inserting or retracting drive unit 204*a*, to form the elongate device 202 into the desired shape.

As shown in FIG. 1213, with the distal segment of the elongate device 202 maintained in the rigid state, a predetermined length of the elongate device 202 may be withdrawn from the stomach S, by translating drive unit 204*a* at the proximal end of elongate device 202, in a retraction direction. Accordingly, the segments of the elongate device 202 proximal to the rigidized distal segment may be repositioned to a location within the stomach S closer to the lesser curvature LC. With the elongate device 202 formed in a rigid desired shape, the medical instrument 226 or other tool may be inserted through the lumen 241 and extend beyond the distal end 218 towards the pyloric sphincter PS. As opposed to pushing against the greater curvature GC of the stomach S and looping, the medical instrument 226 or other tool is pushed against the rigid desired shaped elongate device 202. In other embodiments, the segments proximal to the distal segment, may be actuated into a rigid state to provide more stability to deliver the other tool through the channel 221 without displacing elongate device 202 against the greater curvature GC of the stomach S. As such, the medical instrument 226 or other tool is able to advance within the patient anatomy along a shorter path through the stomach than along the greater curvature GC of the stomach S and without looping of the medical instrument 226 or other tool.

While a particular method of navigation of the stomach S with the elongate device 202 is described above, variations to the method are contemplated by this disclosure. For example, the elongate device 202 may be inserted in a flexible state through the esophagus E, stomach 5, and into the small intestine. As with insertion of traditional flexible elongate devices, the elongate device 202 may loop in the stomach S, taking a non-ideal path. Upon passing the elongate device 202 into the duodenum D, the elongate device 202 will be in a naturally hooked configuration. Upon configuring the distal segment of the elongate device in a rigid state, the hooked configuration provides an anchor for the elongate device 202. For example, the rigid hooked configuration of the elongate device 202 may prevent the distal end 218 of the elongate device 202 from passing back through the pyloric sphincter PS into the stomach S. The segments of the elongate device 202 proximal to the distal segment may be maintained in the flexible state. Accordingly, upon a proximal portion of the elongate device 202 being retracted from the esophagus, the elongate device 202 would be pulled along the stomach wall closer to the esophagus E and pyloric sphincter PS, thereby forming a shorter path to the small intestine than by following the greater curvature GC of the stomach. Upon being configured in the shorter path to the small intestine, one or more of the segments of the elongate device 202 may be configured in a rigid state to maintain the shorter path. The medical instrument 226 or another tool may be inserted through the lumen 241 of the elongate device 202 and be provided to the small intestine via the shorter path. In other embodiments, the elongate device 202 could be positioned in other anatomical targets, organs, or lumens, providing for a desirable path for delivery of other tools.

Figure 12C:
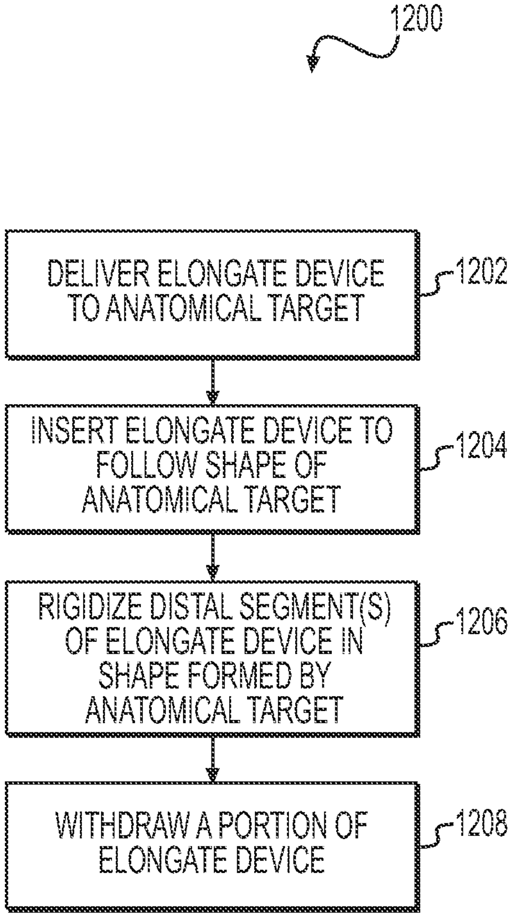
FIG. 12C is a simplified flow diagram showing a method of use of the variable stiffness elongate device for navigate through patient anatomy.

FIG. 12C is a simplified diagram showing a method 1200 of use of the variable stiffness elongate device 202 for navigate through patient anatomy. At 1202, the elongate device 202 is delivered to an anatomical target. Following the example above, the anatomical target may be the stomach S. When positioned at the anatomical target, one or more distal segments of the elongate device 202 may be configured in a flexible state. At 1204, the elongate device 202 is inserted to follow a shape of the anatomical target. For example, the elongate device 202 may follow along a shape of the greater curvature GC of the stomach S to form a "J" shape. At 1206, once conformed to the shape of the anatomical target, one or more distal segments of the elongate device 202 may be maintained in a rigid state. For example, the drive unit 204 may actuate the stiffening mechanism in the one or more distal segments to be configured in a rigid state to maintain the shape of the anatomical target. At 120$, a portion of the elongate device 202 may be withdrawn from the anatomical target while maintaining the one or more distal segments of the elongate device in the rigid state. For example, the elongate device 202 may be withdrawn from the anatomical target until the distal end 218 of the elongate device 202 aligns with a desired path of travel for the medical instrument 226 or other tool inserted through the lumen 241.

Figure 13A:
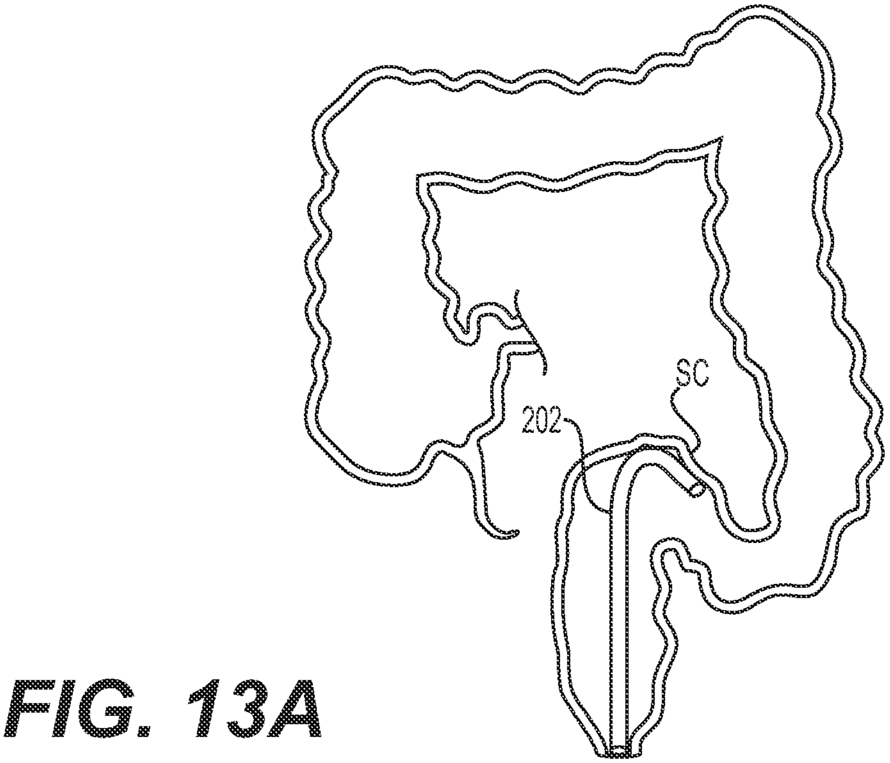
FIGS. 13A-13B are simplified diagrams showing a method of use of the variable stiffness elongate device to optimally navigate through the sigmoid colon of a patient.
Figure 13B:
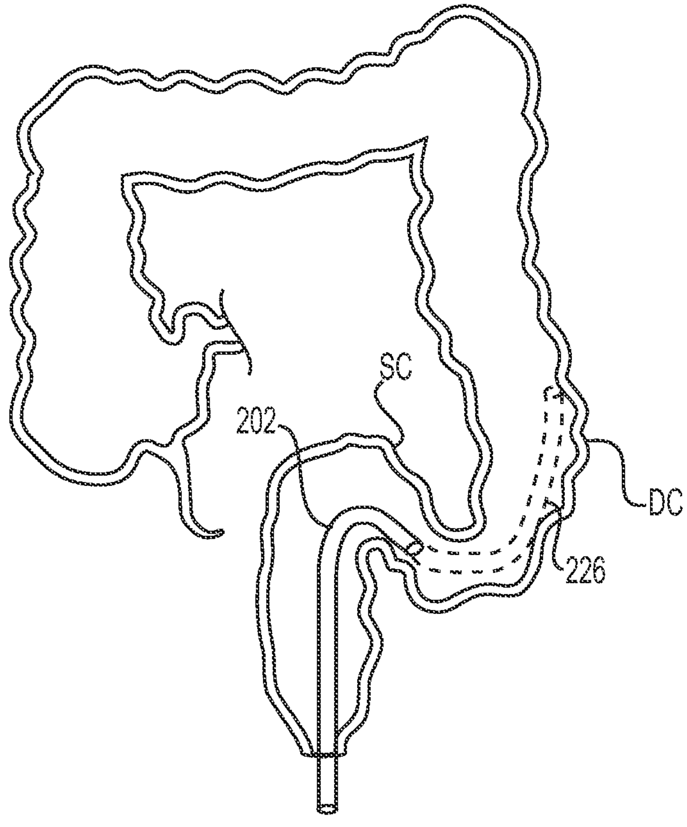

FIGS. 13A-13B are simplified diagrams showing a method of use of the variable stiffness elongate device 202 to optimally navigate through the sigmoid colon SC of a patient. As shown in FIG. 13A, the elongate device 202 is configured in a flexible state and passed into the sigmoid colon SC from the rectum R and the distal end 218 follows along with the shape of a wall along the sigmoid colon SC. Therefore, the distal end 218 of the elongate device 202 conforms to a naturally hooked or "I" shape. With the elongate device 202 positioned in a desired shape, the drive unit 204 may actuate a stiffening mechanism in a distal segment, such as the first segment 506, of the elongate device 202 to be configured in a rigid state to maintain the desired shape. In some implementations, one or more additional segments proximal to the distal segment may additionally be configured in the rigid state. In various implementations, the shape sensor 222 on the elongate device 202 may be used to verify that the elongate device 202 is positioned in the desired shape along the sigmoid colon SC. Based on feedback from the shape sensor 222 an additional length of the elongate device 202 may be passed into the sigmoid colon SC or a length of the elongate device 20:2 may be retracted from the sigmoid colon SC to form the elongate device 202 into the desired shape and potentially flatten out the haustra of colon to optimize the angle of the desired approach to the anatomy in order to perform a task.

As shown in FIG. 13B, with the distal segment of the elongate device 202 maintained in the rigid state, a predetermined length of the elongate device 202 may be withdrawn from the rectum R. Accordingly, the elongate device 202 may maintain a "J" shape at an intermediate location within the sigmoid colon SC. With the elongate device 202 formed in a rigid "J" shape, the medical instrument 226 or other tool may be inserted through the lumen 241 and extend beyond the distal end 218 towards the descending colon DC. As opposed to pushing against the sigmoid colon SC and looping, the medical instrument 226 or other tool is pushed against the rigid "J" shaped elongate device 202. As such, the medical instrument 226 or other tool is able to advance within the patient anatomy along a shorter path through the sigmoid colon SC and without looping of the medical instrument 226 or other tool. While a particular method of navigation of the sigmoid colon SC with the variable stiffness elongate device. 202 is described above, variations to the method are contemplated by this' disclosure.

Use of a Variable Stiffness Flexible Elongate Device for Reducing Folds in Anatomy In addition to assisting in navigation of patient anatomy the elongate device 202 may be used to redirect or straighten patient anatomy. For example, lesions can be hidden within the rugal folds in the stomach or haustra of the colon. Therefore, treatment of the lesions may be assisted by straightening out the rugal folds or haustra folds in the area of a lesion. Likewise, it may be useful to straighten out haustra folds in the colon or a tortuous duodenum to be able to reach farther into patient anatomy or treat an otherwise difficult to reach area. Once anatomy is straight, rigid tools may be used for a therapeutic procedure, if desired.

FIGS. 14A-14D are simplified diagrams showing a method of use of the variable stiffness elongate device 202 with the medical instrument 226 for straightening out or reducing folds in patient anatomy. In the examples shown, the variable stiffness elongate device 202 with the medical instrument 226 are used for straightening out rugal folds in the stomach of a patient. In other examples, the same methods may be performed to straighten out folds in the duodenum, colon, or other anatomy with an irregular or folded surface. For example, the elongate device 202 may be used to straighten or flatten out folds in the duodenum (circular folds) for ablation of hyperplastic mucosal and submucosal layers for treatment of diabetes within the small intestine. Other procedures where it may be desirable to straighten or flatten out anatomy of a patient for performing a therapeutic treatment are contemplated by this disclosure.

Figure 14A:
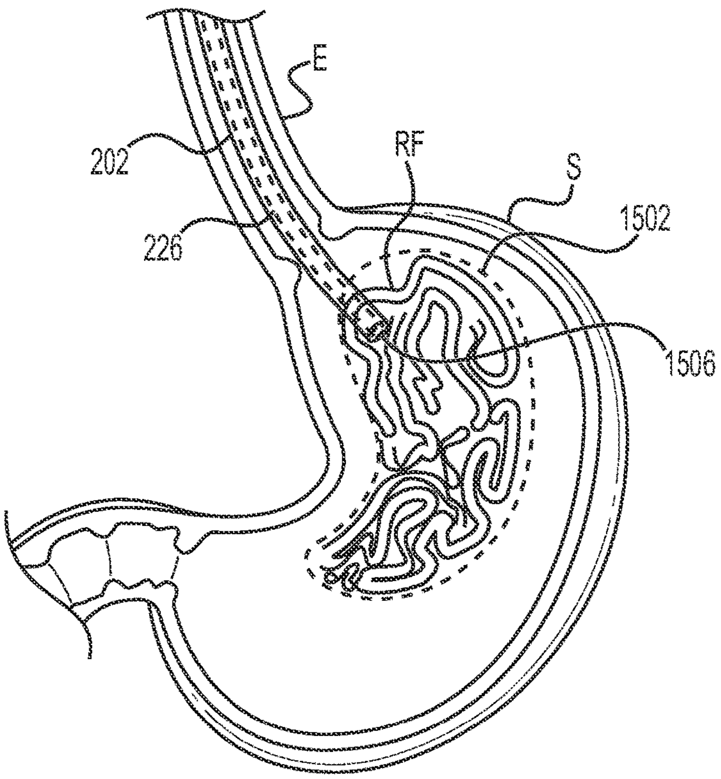
FIGS. 14A-14D are simplified diagrams showing a method of use of the variable stiffness elongate device with the medical instrument for straightening out patient anatomy.

As shown in FIG. 14A, a distal segment of the elongate device 202, such as the first segment 506, is inserted into the stomach S of a patient via the esophagus E and positioned proximate to a target location 1506 within an area 1502 of rugal folds RF on the wall of the stomach S. For example, the medical instrument 226 may be articulated and positioned in the anatomy at the target location 1506. With the medical instrument 226 positioned as desired, the elongate device 202 may be telescopically advanced with or over the medical instrument 226 in a flexible state to conform to a shape of the medical instrument 226.

Upon positioning the distal end 218 of the elongate device 202 in the anatomy at the target location 1506, a distal segment of the elongate device 202 may be configured in a rigid state to maintain the shape. With the distal segment of the elongate device 202 configured in the rigid state, the medical instrument 226 may be withdrawn within the lumen 241 of the elongate device.

Figure 14B:
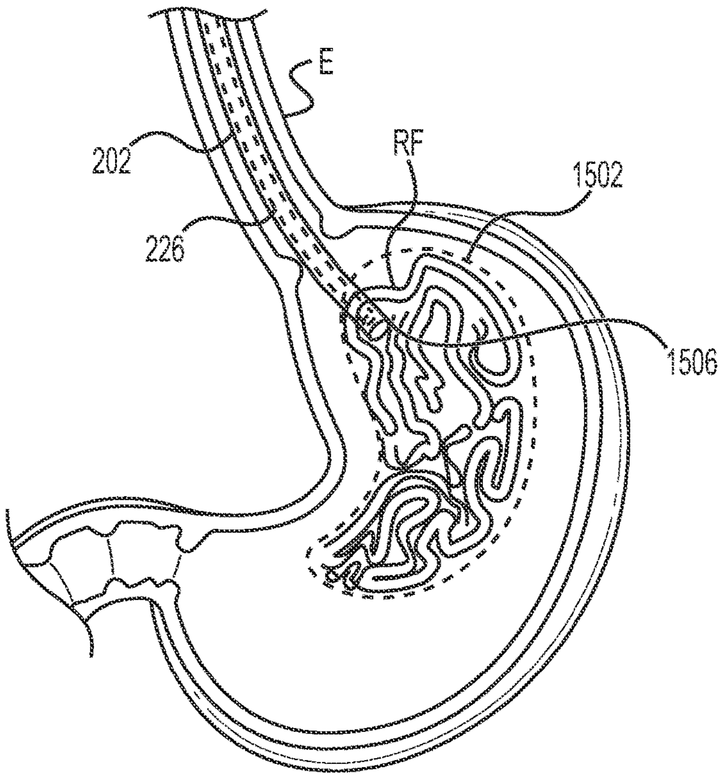

For example, as shown in FIG. 14B, the medical instrument 226 may be withdrawn a short distance within the elongate device 202 so as to no longer maintain contact with the patient anatomy. Once the medical instrument 226 is withdrawn into the elongate device 202, the elongate device may again be configured in a flexible state. With the distal end 218 of the elongate device 202 anchored within the patient anatomy at the target location 1506 and configured in a flexible state, the medical instrument 226 is articulated to move the elongate device 202 along a surface of the patient anatomy to straighten out the surface of the anatomy. With the surface of the anatomy straightened, the distal segment of the elongate device 202 may again be configured in the rigid state to maintain the straightened surface of the anatomy.

Figure 14C:
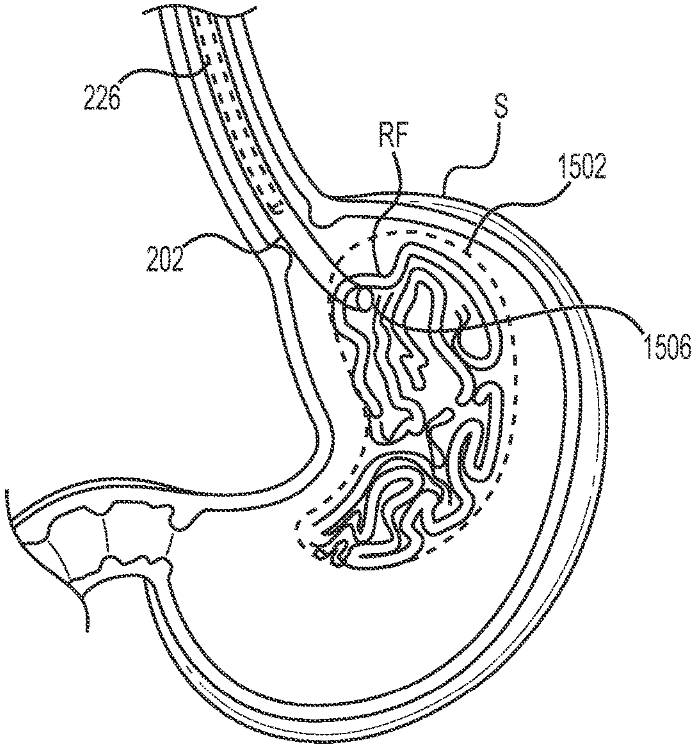
Figure 14D:
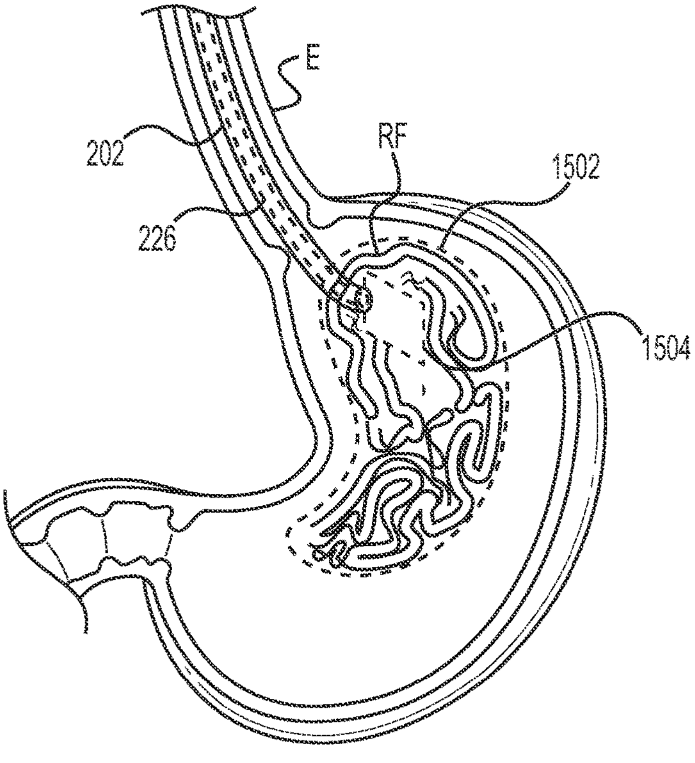
Figure 15A:
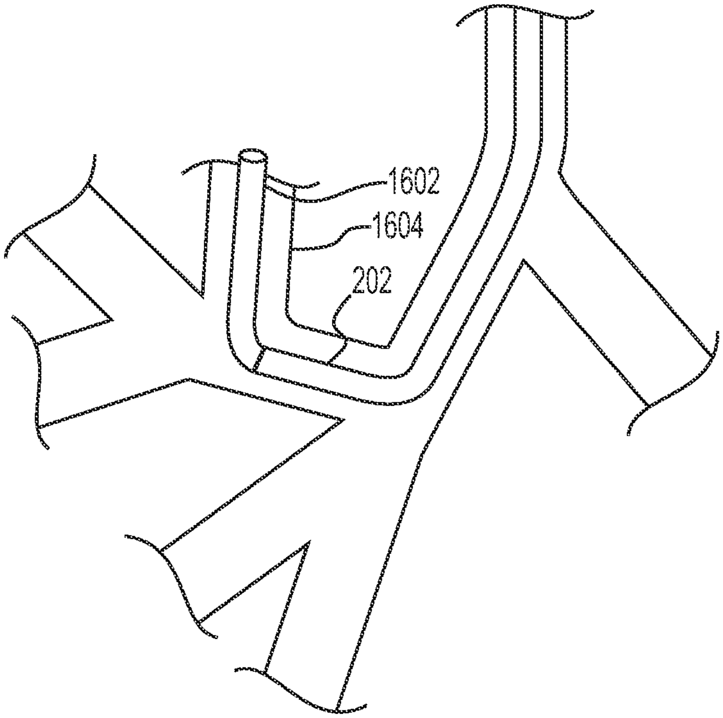
FIGS. 15A-15B are simplified diagrams of showing a method of use of the variable stiffness elongate device with actuation of one or more stiffening mechanisms timed to respiration of a patient.
Figure 15B:
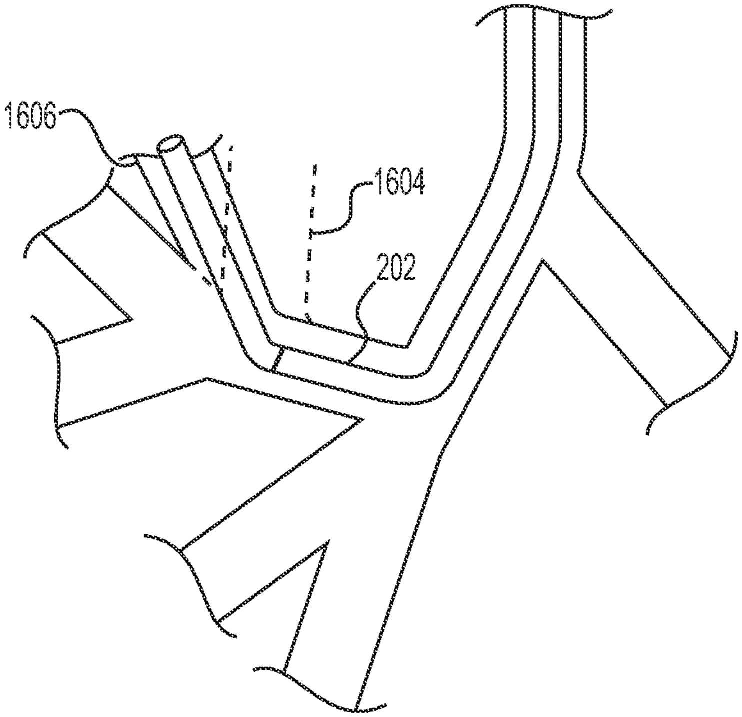

In another example, as shown in FIG. 14C, the medical instrument 226 may be withdrawn a predetermined distance within the elongate device 202, As shown, the predetermined distance is longer than the short distance that the medical instrument 226 is withdrawn in the example of FIG. 15B. Once the medical instrument 226 is withdrawn into the elongate device 202 the predetermined distance, the elongate device may again be configured in a flexible state. With the distal end 218 of the elongate device 202 anchored within the patient anatomy at the target location 1506 and configured in a flexible state, the medical instrument 226 is again inserted through the lumen 241 of the elongate device 202. The force of inserting the medical instrument through the elongate device 202 will cause the elongate device 202 to straighten out along a surface of the patient anatomy. Accordingly, the patient anatomy will likewise be straightened out. With the surface of the anatomy straightened, the distal segment of the elongate device 202 may again be configured in the rigid state to maintain the straightened surface of the anatomy.

In either example, as shown in FIG. 154, the manipulations of the elongate device 202 and the medical instrument will produce an area of straightened anatomy 1504. In the example shown in FIG. 14D, the area of straightened anatomy 1504 is provided among the rugal folds RF of the stomach S.

Figure 14E:
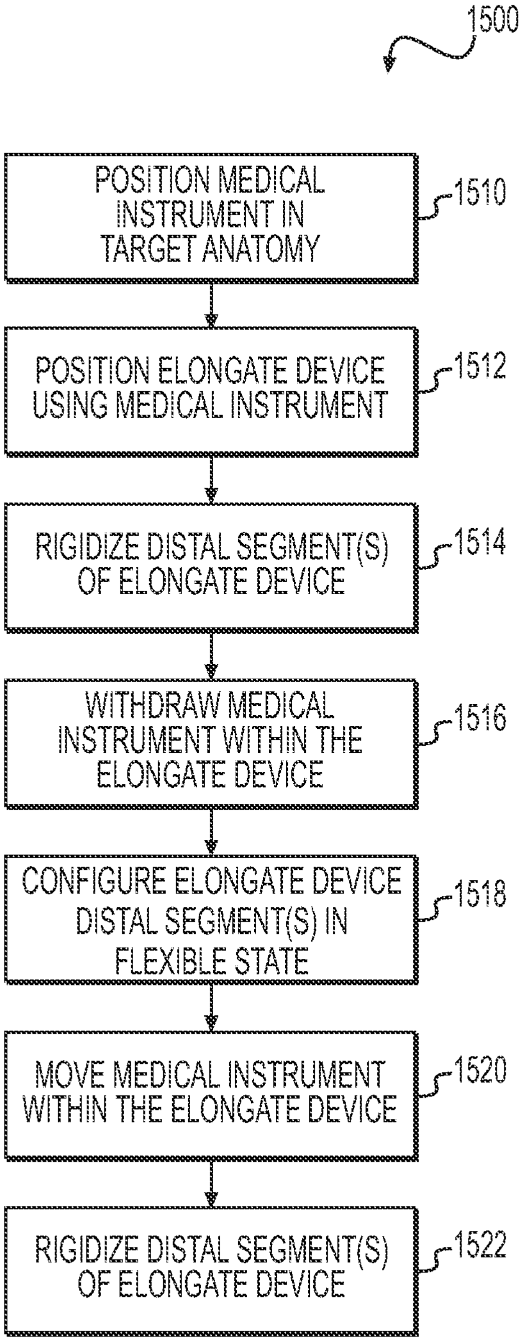
FIG. 14E is a simplified flow diagram showing a method of use of the variable stiffness elongate device for straightening out or reducing folds in patient anatomy.

FIG. 14E is a simplified diagram showing a method 1500 of use of the variable stiffness elongate device 202 for straightening out or reducing folds in patient anatomy. At 1510, the medical instrument 226 is positioned on a surface of target anatomy to be straightened or have folds reduced. The medical instrument 226 may be positioned at a location on the surface of the target anatomy to anchor the medical instrument 226 onto the surface of the target anatomy. At 1512, the elongate device 202 is positioned on the surface of the target anatomy using the medical instrument 226. For example, in the elongate device 202 may have one or more segments configured in a flexible state for following the medical instrument 226 to the surface of target anatomy. For example, the lumen 241 of the elongate device 202 may follow along the medical instrument 226 telescopically. The elongate device 202 may follow the medical instrument 226 until the distal end 218 of the elongate device is positioned at the distal end 228 of the medical instrument 226. Accordingly, the elongate device 202 is anchored on the surface of the target anatomy. At 1514, one or more distal segments, of the elongate device 202 is rigidized to maintain the elongate device 202 anchored on the surface of the target anatomy. For example, the drive unit 204 may actuate the stiffening mechanism in the one or more distal segments to be configured in a rigid state.

At 1516, the medical instrument 226 is withdrawn within the lumen 241 of the elongate device. For example, the medical instrument 226 may be withdrawn a first distance that is a short distance so as to no longer maintain contact with the surface of the target anatomy. In another example, the medical instrument 226 may be withdrawn a second distance that is a predetermined distance longer than the short distance. At 1518, upon the medical instrument 226 being withdrawn within the lumen 241 of the elongate device, one or more distal segments of the elongate device may be configured in a flexible state. For example, the drive unit 204 may actuate the stiffening mechanism in the one or more distal segments of the elongate device 20:2 to be configured in a flexible state.

At 1520, with the one or more distal segments of the elongate device 202 configured in the flexible state, the medical instrument 226 is moved within the lumen 241 of the elongate device 202. For example, when the medical instrument 226 is withdrawn the first distance, a steerable distal end of the medical instrument 226 may be articulated to move both the medical instrument 226 and the one or more distal segments of the elongate device 202. The movement of the elongate device 202 along the surface of the target anatomy thereby straightens out or reduces folds on the target anatomy. When the medical instrument 226 is withdrawn the second distance, the medical instrument 226 may be inserted through the lumen 241 of the elongate device 202. The force of inserting the medical instrument through the elongate device 202 will cause the elongate device 202 to straighten out along the surface of the target anatomy. At 1522, the one or more distal segments of the elongate device 202 are once again rigidized to maintain the surface of the target anatomy straightened or with reduced folds.

While some example methods of using the elongate device 202 and the medical instrument 226 are described above, other methods are contemplated by this disclosure. For example, the medical instrument 226 may be positioned at a target location in patient anatomy while the elongate device is maintained in the flexible state. Upon reaching the target location, the medical instrument 226 may be articulated into a hook or spiral and pulled hack to cause the elongate device 202 to buckle. A distal end of the medical instrument 226 may be anchored in the anatomy at the target location. Upon the elongate device 20:2 buckling, one or more segments of the elongate device are configured in a rigid state, thereby causing the elongate device 202 to extend proximally and stretch out the anatomy at the target location. Other methods of straightening out anatomy with a variable stiffness elongate device 202 are contemplated by this disclosure.

Use of a Variable Stiffness Flexible Elongate Device Synchronized with Respiration, Circulation, or Excretion In various embodiments described throughout this disclosure, the variable stiffness elongate device 202 is positioned in anatomy which may apply an external force against the flexible body 216. For example, external forces may be applied to anatomy by the flexible body when in a rigidized state due to changes in anatomy as part of respiration, circulation, or excretion. The control system 112 can receive sensor data from one or more sensors positioned along the flexible body 216 for detecting application of an external force. Force sensors positioned along the flexible body 215 may include one or more of a strain gauge, a load cell, a force sensing resistor, or any other suitable force sensor. Each of the force sensors may correspond to a particular location, region, or segment of the flexible body 216. Using selective discrete stiffening control of the embodiments above, upon detecting an external force at a location at a distal end or along the length of the flexible body 216, the control system 112 can command the drive unit 204 to selectively stiffen discrete portions along the length of the flexible body 216 at the location of the external force. For example, the control system 112 determines whether any of the received sensor data is out of a predetermined threshold for identifying application of an external force.

Additionally or alternatively to detecting external forces with sensor(s) along the flexible body 216, the control system 112 can command the drive unit 204 to selectively stiffen discrete portions along the length of the flexible body 216 based on one or more external sensors that detect a rhythm or signal associated with respiration, circulation, or excretion. For example, the control system 112 may receive a signal from a respirator (e.g., respiratory rate and/or tidal volume), a heartbeat monitor, one or more sensors for detecting peristalsis, such as by monitoring the basal electrical rhythm in one or more sections of the gastrointestinal tract, and/or other sensors for monitoring physiological rhythms of a patient.

Shape sensing can be used to determine which segments 224 of the flexible body 216 is/are experiencing an external force. Additionally or alternatively, shape sensing can be used in conjunction with a registered pre-operative model where target areas of anatomy have been previously identified, to determine whether a portion (or plurality of portions) of the flexible body 216 is/are experiencing external force based on the current positioning of the flexible body 216 in anatomy. The control system 112 can then selectively activate discrete stiffening elements to selectively stiffen portions of the flexible body 216 located at the determined portions of the flexible body 216.

FIGS. 15A-16C are simplified diagrams of showing a method of use of the variable stiffness elongate device 202 with actuation of one or more stiffening mechanisms timed to cyclical motion caused by respiration, peristalsis, circulation, or excretion.

FIGS. 15A-15B are simplified diagrams of showing a method of use of the variable stiffness elongate device 202 with actuation of one or more stiffening mechanisms timed to respiration of a patient with the elongate device 202 positioned within airways of a patient lung. As shown in FIG. 15A, a distal segment 1602 of the elongate device 202, such as the first segment 506, is inserted into an airway of a patient. The airway may initially be positioned at a first location 1604. However, as shown in FIG. 15B, during respiration, the airway may move to a second location 1606. In an effort to reduce stretching or other strain on airways, actuation of a stiffening mechanism in the distal segment 1602 of the elongate device 202 may be timed to respiration of the patient. For example, when the airway is at the first location 1604, the stiffening mechanism in the distal segment 1602 may be actuated to be configured in a rigid state to facilitate further navigation of the airway or performing a therapeutic procedure in the airway. Upon detecting a cycle in the respiration of the patient, the stiffening mechanism in the distal mechanism may be actuated to be configured in a flexible state. Therefore, as shown in FIG. 16B, the distal segment 1602 of the elongate device 202 may conform with the motion of the airway during respiration. While the stiffening mechanism in the distal segment 1602 is actuated with the timing of respiration of the patient, stiffening mechanisms in one or more additional segments proximal to the distal segment 1602 may additionally or alternatively be actuated with the respiration of the patient.

Figure 16A:
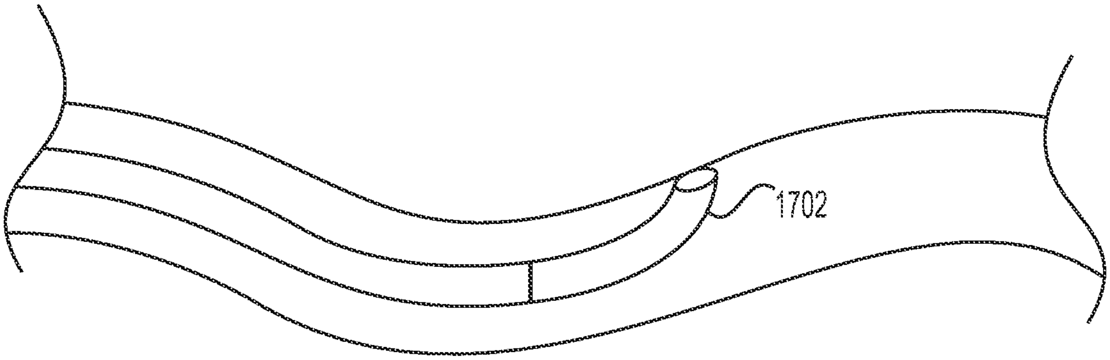
FIGS. 16A-16C are simplified diagrams of showing a method of use of the variable stiffness elongate, device with actuation of one, or more stiffening mechanisms timed to peristalsis within the gastrointestinal tract of a patient.
Figure 16B:
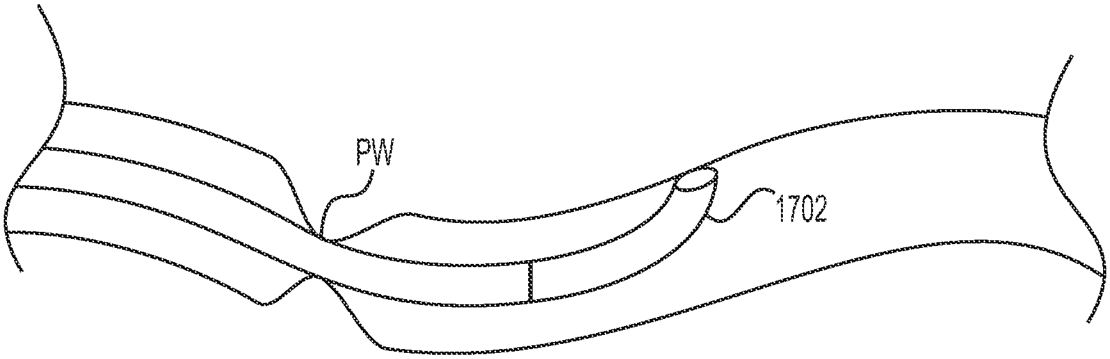
Figure 16C:
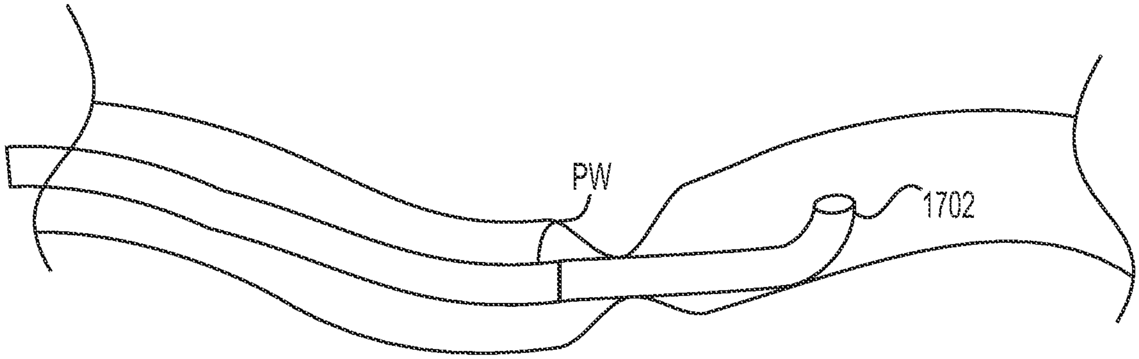

FIGS. 16A-16C are simplified diagrams of showing a method of use of the variable stiffness elongate device 202 with actuation of one or more stiffening mechanisms timed to peristalsis within the gastrointestinal tract of a patient. As shown in FIG. 16A, a distal segment 1'702 of the elongate device 202, such as the first segment 506, is inserted into portion of the gastrointestinal tract of a patient. The distal segment 1702 may be positioned in a pose and configured in a rigid state to facilitate a therapeutic procedure at a target location. Using registration of the flexible elongate device 202 and real time tracking, and by identifying the target location in the gastrointestinal tract, the flexible body 216 can be parked at the target location. For example, a virtual navigational image in which the actual location of the distal segment 170:2 is registered (i.e., dynamically referenced) with a preoperative or concurrent image/model. Alternatively or additionally, control system 112 may also store a reading from the shape sensor 222 indicative of the shape of the elongate device 202 when parked at the target location.

As shown in FIG. 16B, a peristaltic wave PW may periodically pass along a length of the gastrointestinal tract in the vicinity of the target location. As discussed above, the control system 112 may detect the peristaltic wave PW with one or more sensors that monitor the basal electrical rhythm in a section of the gastrointestinal tract containing the target location. As the peristaltic wave PW approaches the distal segment 1702, the drive unit 204 actuates the stiffening mechanism in the distal segment 1702 to be configured in a flexible state. Therefore, as shown in FIG. 16C, as the peristaltic wave passes over the distal segment 1702, the elongate device 20:2 may conform to the motions of the peristaltic wave PW. Upon the peristaltic wave PW passing beyond the distal segment 1702, the distal segment 1702 may once again return to the pose shown in FIG. 17A and be configured in a rigid state at the target location to resume the therapeutic procedure.

While the examples shown are for timing actuation of one or more stiffening mechanism in the elongate device 202 in an airway or in the gastrointestinal tract, other examples are contemplated by this disclosure. For example, the same methods described herein can likewise be performed within vasculature of a patient. In another example, actuation of one or more stiffening mechanisms of the elongate device 202 may be timed to move with the heart beat during ablation for atrial fibrillation (AFIB) treatment. In another example, actuation of one or more stiffening mechanisms of the elongate device 202 may be timed to aid in targeted deployment of a fenestrated endograft during endovascular in the setting of aneurysm repair. Other examples are contemplated by this disclosure.

In the examples discussed above, the stiffening mechanism is periodically configured between a rigid and a flexible state, or vice versa. Such periodic configuration of a balloon stiffening mechanism may be facilitated by application of an inflation pressure or vacuum from a pump timed to cyclical motion caused by respiration, peristalsis, circulation, or excretion. In another example, periodic configuration of a nitinol wire stiffening mechanism may be facilitated by application of energy or current to the nitinol wire timed to cyclical motion caused by respiration, peristalsis, circulation, or excretion. In a further example, periodic configuration of a control wire stiffening mechanism may be facilitated by application of tension or slack to the control wire timed to the cyclical motion caused by respiration, peristalsis, circulation, or excretion.

Figure 17:
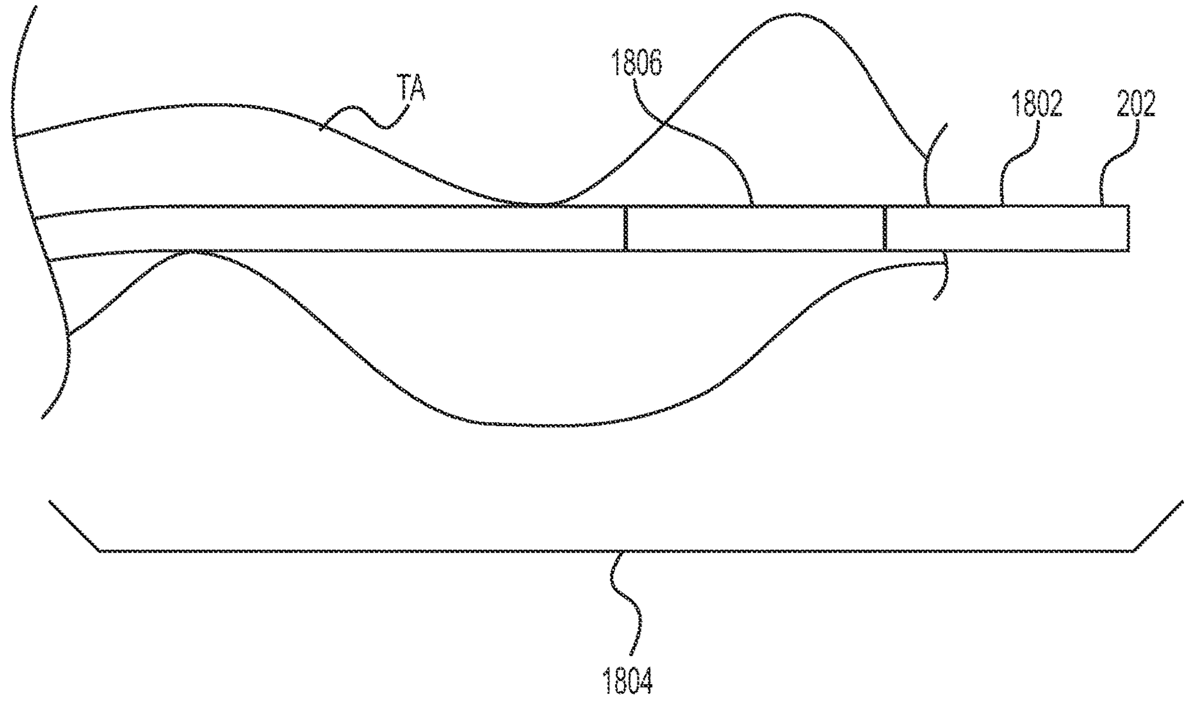
FIG. 17 is a simplified diagram of showing a method of use of the variable stiffness elongate device with stiffening mechanism(s) in one or more distal segments of the elongate device configured in a rigid state to facilitate pushing through the tortuous anatomy.

Use of a Variable Stiffness Flexible Elongate Device for Rigid Navigation of Tortuous Anatomy As discussed above, navigation of tortuous anatomy may lead to looping of flexible elongate devices due to friction between the wall of the tortuous anatomy and the elongate device. FIG. 17 is a simplified diagram of showing a method of use of the variable stiffness elongate device 202 with stiffening mechanism(s) in one or more distal segments of the elongate device 202 configured in a rigid state to facilitate linearly pushing through the tortuous anatomy. As shown in FIG. 17, a distal segment 1802 of the elongate device 202, such as the first segment 506, is positioned at a section of tortuous anatomy TA. For example, the distal segment 1802 may be positioned at the beginning of the section of tortuous anatomy TA. The drive unit 204 may actuate a stiffening mechanism in the distal segment 1802 to be configured in a rigid state. Accordingly, as the elongate device 202 is advanced into the tortuous anatomy, the distal segment 1802 will follow a linear path forward as opposed to following the tortuous path of the anatomy.

As a segment proximal to the distal segment ("second segment 1806") is positioned at the beginning of the section of tortuous anatomy, the drive unit 204 may configure a stiffening mechanism in the second segment 1806 to be configured in a rigid state. Accordingly, both the distal and the second segments 1802, 1806 may be advanced linearly through the tortuous anatomy. Additional proximal segments may likewise have corresponding stiffening mechanisms configured in the rigid state as they are positioned at the beginning of the section of tortuous anatomy. Therefore, a rigid length of a plurality of segments along a distal section 1804 of the elongate device 202 may be formed for linearly advancing through the section of tortuous anatomy as oppose to following the tortuous path of the anatomy. While stiffening mechanism(s) in one or more segments in the distal section 1804 of the elongate device 202 are actuated to be configured in a rigid state, stiffening mechanism(s) in one or more segments proximal the distal section 1804 may be actuated to be configured in a flexible state.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, while particular aspects of the elongate device 202 are described separately under discrete headings, the various features, elements, components, or methods may be combined or integrated in another system or certain features may be omitted or not implemented.

Also, techniques, systems, subsystems, and methods discretely or separately described under different headings and illustrated in different drawings in the various embodiments may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

ADDITIONAL EXAMPLES

1. A method of navigating a patient anatomy using an elongate, variable stiffness device having a proximal end, a distal end, and a plurality of segments positioned along a length of the variable stiffness device, the elongate device defining a first lumen through the plurality of segments, wherein each of the plurality of segments is individually configurable between a rigid state and a flexible state, the method comprising:
   maintaining a segment of the plurality of segments at the distal end of the variable stiffness device in the flexible state as the segment is advanced along a flexible elongate instrument within the first lumen, wherein the flexible elongate instrument is positioned at a first location in the patient anatomy;

selectively rigidizing the segment to the rigid state upon reaching a location along the flexible elongate instrument;

maintaining the segment in the rigid state as the flexible elongate instrument is advanced through the first lumen to a second location such that a distal end of the flexible elongate instrument extends beyond the segment at the distal end of the variable stiffness device.

2. The method of example 1, wherein the distal end of the flexible elongate instrument is steerable, wherein the steerable distal end is maintained in a pose in a direction for navigation of a section of the patient anatomy while the segment is advanced along the flexible elongate instrument.

3. The method of example 2, wherein the segment conforms to the shape of the flexible elongate instrument as the segment is advanced along the flexible elongate instrument in the flexible state.

4. The method of example 1, wherein selectively rigidizing the segment to the rigid state comprises configuring actuation of a stiffening mechanism in the segment to transition from the flexible state to the rigid state.

5. The method of example 4, wherein the stiffening mechanism is a balloon, a nitinol wire, or a control wire.

6. The method of example 1, wherein the location along the flexible elongate instrument is where the distal end of the variable stiffness device is a predetermined distance beyond the distal end of the flexible elongate instrument.

7. The method of example 1, wherein the location along the flexible elongate instrument is where the distal end of the variable stiffness device is proximate to the distal end of the flexible elongate instrument.

8. The method of example 1, further comprising:

selectively transitioning the segment from the rigid state to the flexible state upon the flexible elongate instrument reaching the second location;

maintaining the segment in the flexible state as the segment is advanced along the flexible elongate instrument at the second location.

9. The method of example 1, further comprising:

maintaining a second segment of the plurality of segments in the rigid state, wherein the second segment is proximal to the segment.

10. The method of example 9, wherein the second segment is maintained in the rigid state as the segment is advanced along the flexible elongate instrument.

11. The method of example 9, wherein the second segment is maintained in the rigid state at a third location in the patient anatomy, the method further comprising:

selectively rigidizing a third segment of the plurality of segments to the rigid state upon reaching the third location as the variable stiffness device is advanced within the patient anatomy, wherein the third segment is proximal to the second segment.

12. The method of example 11, further comprising:

selectively transitioning the second segment from the rigid state to the flexible state upon the second segment advancing beyond the third location in the patient anatomy.

13. The method of example 11, wherein the third location in the patient anatomy is a predefined target area in the patient anatomy.

14. The method of example 13, wherein the predefined target area in the patient anatomy is identified on a virtual image of the variable stiffness device integrated into a pre-operative model of the patient anatomy.

15. The method of example 14, further comprising:

updating the virtual image of the variable stiffness device based on real-time positioning information of the variable stiffness device in the patient anatomy.

16. The method of example 13, wherein the target area in the patient anatomy is a location proximate to a potential prolapse.

17. The method of example 9, wherein the second segment is maintained in a second pose, and wherein the distal end of the flexible elongate instrument is steerable, the method further comprising:

selectively transitioning the second segment from the rigid state to the flexible state upon the flexible elongate instrument being withdrawn through the first lumen to the second segment;

maintaining the second segment in the flexible state as the flexible elongate instrument is positioned in an adjusted second pose;

selectively rigidizing the second segment to the rigid state upon conforming to the adjusted second pose.

18. The method of example 2, wherein the first location in the patient anatomy is at an intermediate location in the stomach between the lesser and greater curvature of the body of the stomach.

19. The method of example 18, wherein the pose is a "J" shape in a direction of the pyloric sphincter.

20. The method of example 19, wherein the location along the flexible elongate instrument is where the distal end of the variable stiffness device is positioned beyond the pyloric sphincter within the duodenum.

21. The method of example 2, wherein the first location in the patient anatomy is within the duodenum proximate to the major duodenal papilla.

22. The method of example 21, wherein the pose is in a direction of the major duodenal papilla at an angle of approach to facilitate cannulation of the common bile duct while avoiding cannulation of the pancreatic duct.

23. The method of example 22, further comprising:

verifying that the angle of approach is accurate based on a shape sensor on the variable stiffness device or the flexible elongate instrument.

24. The method of example 22, wherein the cannulation of the common bile duct is performed as part of an endoscopic retrograde cholangiopancreatography.

25. The method of example 2, wherein the first location in the patient anatomy is in the bladder between the urethral orifice and the ureterovesical junction.

26. The method of example 25, wherein the pose is in a direction of the ureterovesical junction to facilitate cannulation of a ureter.

27. The method of example 22, wherein the cannulation of the ureter is performed as part of a ureteroscopy.

28. The method of example 2, wherein the first location in the patient anatomy is in the renal pelvis proximate to a target major calyx.

29. The method of example 28, wherein the pose is in a direction of the target major calyx.

30. The method of example 29, wherein the target major calyx is in a lower portion of the kidney.

31. The method of example 1, wherein the flexible elongate instrument comprises a second lumen, wherein the lumen or the second lumen provide a conduit for a treatment tools for use in a therapeutic procedure.

32. The method of example 1, further comprising:
selectively transitioning the segment from the rigid state to the flexible state to be removed after treatment of the patient anatomy.

33. A method of navigating a portion of patient anatomy using an elongate, variable stiffness device having a proximal end, a distal end, and a plurality of segments positioned along a length of the variable stiffness device, wherein one or more of the plurality of segments is individually configurable between a rigid state and a flexible state, the method comprising:
maintaining a segment of the plurality of segments at the distal end of the variable stiffness device in the flexible state as the segment is advanced from an entry point of the portion of the patient anatomy to a sidewall of the portion of the patient anatomy opposite from the entry point and along the sidewall to conform to a desired shape;
selectively rigidizing the segment to the rigid state upon conforming to the desired shape; and
maintaining the segment in the rigid state as variable stiffness device is withdrawn from the entry point to a position with the segment in the desired shape for navigating the patient anatomy.

34. The method of example 33, wherein the portion of the patient anatomy is a hollow cavity anatomy selected from the group comprising the stomach, the colon, the bladder, and the heart.

35. The method of example 33, wherein the variable stiffness device defines a lumen through the plurality of segments, wherein the lumen provides a conduit for receiving a flexible elongate instrument for use in a therapeutic procedure.

36. The method of example 35, wherein the patient anatomy is the stomach, the entry point is the esophagus, and the sidewall is the greater curvature of the stomach.

37. The method of example 36, wherein the position is at an intermediate location in the stomach between the lesser and greater curvature of the body of the stomach such that the desired shape points in a direction of the pyloric sphincter.

38. The method of example 35, wherein the patient anatomy is the sigmoid colon, the entry point is the rectum, and the sidewall is a wall of the colon.

39. The method of example 38, wherein the position is at an intermediate position in the sigmoid colon such that the desired shape points in a direction of the descending colon.

40. The method of example 35, wherein the patient anatomy is the bladder, the entry point is the urethral orifice, and the sidewall is a wall of the bladder.

41. The method of example 40, wherein the position is at an intermediate position in the bladder such that the desired shape points in a direction of a ureterovesical junction.

42. The method of example 35, wherein the desired shape is a "J" shape for navigating the flexible elongate instrument through the portion of the patient anatomy without looping.

43. The method of example 33, further comprising:
verifying whether the segment conforms to the desired shape based on feedback from a shape sensor positioned along a length of the variable stiffness device.

44. A method of maintaining a position of an elongate, variable stiffness device within patient anatomy, the variable stiffness device having a proximal end, a distal end, and a plurality of segments positioned along a length of the variable stiffness device, wherein one or more of the plurality of segments is individually configurable between a rigid state and a flexible state, the method comprising:
maintaining a segment of the plurality of segments at the distal end of the variable stiffness device in the rigid state in a preconfigured shape for performing a therapeutic procedure in the patient anatomy;
detecting motion of the patient anatomy from a first location to a second location;
selectively transitioning the segment from the rigid state to the flexible state in response to the detected motion of the patient anatomy; and
selectively transitioning the segment from the flexible state to the rigid state subsequent to the motion of the patient anatomy upon the segment returning to the preconfigured shape.

45. The method of example 44, wherein the motion of the patient anatomy is cyclical.

46. The method of example 45, wherein the motion is due to respiration, circulation, or excretion motion is cyclical.

47. The method of example 46, wherein the motion of the patient anatomy is detected by a force or shape sensor.

48. The method of example 46, wherein the motion of the patient anatomy is detected based on a signal from a sensor for monitoring physiological rhythms of a patient.

49. The method of example 48, wherein, the sensor is a respirator, a heartbeat monitor, or a sensor for detecting peristalsis.

50. The method of example 45, wherein selectively transitioning the segment from the rigid state to the flexible state is timed to match the cyclical motion of the patient anatomy.

51. A method of redirecting patient anatomy using a steerable, elongate instrument and a variable stiffness device, the method comprising:
maintaining a segment at a distal end of the rigidizable device in a flexible state as the segment is advanced telescopically with the steerable instrument to conform the variable stiffness device to a shape of the steerable instrument, wherein the steerable instrument is positioned in the patient anatomy at a target location;
transitioning the segment to a rigid state when a distal tip of the rigidizable device is at a distal tip of the steerable instrument in the patient anatomy at the target location;
maintaining the segment in the rigid state as the steerable instrument is withdrawn predetermined distance from the distal tip of the rigidizable device;
transitioning the segment to the flexible state upon the steerable instrument being withdrawn the predetermined distance;
maintaining the segment in the flexible state as the steerable instrument is moved to redirect the patient anatomy with the rigidizable device to a redirected location; and
transitioning the segment to the rigid state to maintain the patient anatomy at the redirected location.

52. The method of example 51, wherein the rigidizable device is carried by steerable instrument.

53. The method of example 51, wherein the rigidizable device is delivered along steerable instrument.

54. The method of example 51, wherein the rigidizable device delivered over steerable instrument.
55. The method of example 51, wherein the patient anatomy is a fold within the stomach shish s straightened in the redirected location.
56. The method of example 51, wherein the patient anatomy is a fold within the colon which is straightened in the redirected location.
57, The method of example 51, wherein t steerable instrument is moved by advancing the steerable instrument while the segment is in the flexible state.
58. The method of example 51, wherein the steerable instrument is moved by articulating the steerable instrument while the segment is in the flexible state.
59. A method of anchoring a variable stiffness device in a patient anatomy for performance of a therapeutic procedure, the method comprising:
   maintaining a segment at a distal end of the rigidizable device in a flexible state as the segment is positioned in the patient anatomy proximate to a location of the therapeutic procedure;
   receiving a guide to conform the segment into an anchor shape; and
   transitioning the segment to a rigid state in the anchor shape to lock the segment into anatomy at the location.
60. The method of example 59, further comprising:
   receiving art elongate instrument for performing the therapeutic procedure through a working lumen in the rigidizable device.
61. The method of example 60, wherein the patient anatomy is an airway, the elongate instrument is an ablation probe, and anchor shape locks the segment in the anatomy in a direction of a tumor.
62. The method of example 61, wherein the segment is maintained in the rigid state in the anchor shape while the ablation probe punctures the airway.
63. The method of example 60, wherein the instrument is a high velocity fluid delivery tool, and the anchor shape locks the segment in the anatomy to prevent deforming of the high velocity fluid delivery tool during delivery of high velocity fluids.
64. The method of example 60, wherein the patient anatomy is a gastrostomy and the anchor shape locks the segment in the stomach at an optimized angle of approach to treat target tissue.
65. The method of example 64, wherein the target tissue is necrotic tissue or cysts in the pancreas.
66. The method of example 64, wherein the target tissue is the gall bladder.

What is claimed is:

1. A system, comprising:
an elongate device having a proximal end, a distal end, a plurality of segments positioned along a length of the elongate device between the proximal end and the distal end, and stiffening mechanisms, each of the stiffening mechanisms configured to selectively alter rigidity of one or more of the plurality of segments; and
a flexible elongate instrument having a proximal end and a distal end, wherein one of the elongate device or the flexible elongate instrument includes a lumen and the other of the elongate device or the flexible elongate instrument is configured to be slidably disposed within the lumen for telescopic operation.

2. The system of claim 1, further comprising:
a drive unit configured to control one or more of the stiffening mechanisms to maintain a pose of the elongate device during telescopic operation with the flexible elongate instrument.

3. The system of claim 2, wherein the drive unit is coupled to the proximal end of the elongate device and configured to actuate insertion or retraction of the elongate device along an insertion axis.

4. The system of claim 3, further comprising:
an instrument drive unit coupled to the proximal end of the flexible elongate instrument and configured to actuate insertion or retraction of the flexible elongate instrument along the insertion axis for the telescopic operation.

5. The system of claim 2, wherein the drive unit is configured to control individual actuation and operation of each of the stiffening mechanisms.

6. The system of claim 2, wherein the lumen extends through the elongate device, wherein the distal end of the flexible elongate instrument is steerable to establish the pose, and wherein the drive unit is configured to control one or more of the stiffening mechanisms to be in a flexible state during insertion of the elongate device along the flexible elongate instrument such that the elongate device conforms to the pose established by the steerable distal end of the flexible elongate instrument.

7. The system of claim 2, wherein the pose of the elongate device is established by a natural shape of patient anatomy or a wire shaped into a shape of the pose.

8. The system of claim 2, wherein the drive unit is further configured to control timing of actuation of one or more of the stiffening mechanisms to cyclical motion caused by respiration, peristalsis, circulation, or excretion.

9. The system of claim 1, wherein one or more of the stiffening mechanisms is configurable between a plurality of rigidity states along a spectrum from partially rigid to fully rigid.

10. The system of claim 1, wherein one or more of the stiffening mechanisms is configured to alter rigidity of a group of the plurality of segments.

11. A method of using an elongate device having a proximal end, a distal end, a plurality of segments positioned along a length of the elongate device, a lumen that extends through the plurality of segments, and stiffening mechanisms, each of the stiffening mechanisms configured to selectively alter rigidity of one or more of the plurality of segments between a rigid state and a flexible state, the method comprising:
conforming the elongate device to a desired shape while one or more of the stiffening mechanisms are maintained in a flexible state;
controlling one or more of the stiffening mechanisms to maintain the elongate device in the desired shape; and
telescopically sliding an elongate instrument along the lumen while the elongate device maintains the desired shape.

12. The method of claim 11, further comprising:
steering a distal end of the elongate instrument to establish the desired shape,
wherein conforming the elongate device to the desired shape comprises telescopically sliding the elongate device over the distal end of the elongate instrument with the desired shape.

13. The method of claim 11, wherein conforming the elongate device to the desired shape comprises positioning the elongate device to conform to a natural shape of patient anatomy.

14. The method of claim 11, wherein conforming the elongate device to the desired shape comprises receiving a wire shaped into the desired shape through the lumen.

15. The method of claim 11, further comprising:

controlling timing of actuation of one or more of the stiffening mechanisms to cyclical motion caused by respiration, peristalsis, circulation, or excretion.

16. The method of claim 11, further comprising:

using one or more tools of the elongate instrument to perform a therapeutic or diagnostic procedure while the elongate device maintains the desired shape.

17. The method of claim 16, wherein the one or more tools includes a cutting tool, an ablation tool, an imaging tool, a high velocity fluid delivery tool, or another tool for performing a therapeutic or diagnostic procedure.

18. The method of claim 11, wherein the desired shape maintains the elongate device as an anchor in patient anatomy.

19. The method of claim 11, wherein one or more of the stiffening mechanisms is configurable between a plurality of rigidity states along a spectrum from partially rigid to fully rigid.

20. The method of claim 11, further comprising:

forming a rigid length of a subset of the plurality of segments along a distal section of the elongate device; and linearly advancing the elongate device through a section of tortuous anatomy.

* * * * *